(12) United States Patent
Jeney et al.

(10) Patent No.: US 7,993,881 B2
(45) Date of Patent: Aug. 9, 2011

(54) METHOD FOR DETECTING PATHOGENS USING MOLECULAR BEACONS

(75) Inventors: Csaba Jeney, Budapest (HU); Tibor Takacs, Pilisjaszfalu (HU)

(73) Assignee: Genoid Kft, Budapest (HU)

( * ) Notice: Subject to any disclaimer, the term of this patent is extended or adjusted under 35 U.S.C. 154(b) by 0 days.

(21) Appl. No.: 12/093,878

(22) PCT Filed: Nov. 15, 2006

(86) PCT No.: PCT/GB2006/004266
§ 371 (c)(1),
(2), (4) Date: Jan. 21, 2009

(87) PCT Pub. No.: WO2007/057669
PCT Pub. Date: May 24, 2007

(65) Prior Publication Data
US 2009/0215030 A1    Aug. 27, 2009

Related U.S. Application Data

(60) Provisional application No. 60/737,006, filed on Nov. 15, 2005.

(30) Foreign Application Priority Data

Nov. 15, 2005    (GB) .................................. 0523250.9

(51) Int. Cl.
*C12P 19/34* (2006.01)
*C12Q 1/68* (2006.01)
*C07H 21/04* (2006.01)

(52) U.S. Cl. ....... 435/91.2; 435/6; 536/23.1; 536/24.32; 536/24.33

(58) Field of Classification Search ........................ None
See application file for complete search history.

(56) References Cited

U.S. PATENT DOCUMENTS

| | | | |
|---|---|---|---|
| 6,037,130 A * | 3/2000 | Tyagi et al. ........................ 435/6 |
| 6,159,729 A | 12/2000 | Hofmann et al. | |
| 6,713,262 B2 * | 3/2004 | Gellibolian et al. .............. 506/4 |
| 2002/0102571 A1 | 8/2002 | Theaker et al. | |
| 2003/0068625 A1 | 4/2003 | Sheehan et al. | |
| 2004/0151723 A1 | 8/2004 | Maeda et al. | |
| 2005/0176023 A1 * | 8/2005 | Ramon et al. ...................... 435/6 |
| 2005/0215497 A1 | 9/2005 | Harel-Bellan et al. | |

FOREIGN PATENT DOCUMENTS

| | | |
|---|---|---|
| EP | 0477972 | 9/1991 |
| EP | 1201771 | 5/2002 |
| WO | WO 93/00435 | 1/1993 |
| WO | WO 01/09386 | 2/2001 |
| WO | WO 03/000933 | 1/2003 |
| WO | WO 03/057914 | 7/2003 |
| WO | WO 03/076667 | 9/2003 |
| WO | WO 2005/033333 | 4/2005 |

OTHER PUBLICATIONS

El-Hajj et al. Detection of Rifampin Resistance in Mycobacterium tuberculosis in a Single Tube with Molecular Beacons. Journal of Clinical Microbiology (2001) 39(11): 4131-4137.*
Vet et al. Multiplex detection of four pathogenic retroviruses using molecular beacons. Proceedings of the National Academy of Sciences, USA (1999) 96: 6394-6399.*
Rys et al. Preventing False Positives: Quantitative Evaluation of Three Protocols for Inactivation of Polymerase Chain Reaction Amplification Products. Journal of Clinical Microbiology (1993) 31(9): 2356-2360.*
Caparros-Wanderley et al. Intratype sequence variation among clinical isolates of the human papillomavirus type 6 L1 ORF: clustering of mutations and identification of a frequent amino acid sequence variant. Journal of General Virology (1999) 80: 1025-1033.*
GenBank Accession No. AF067160.1 for the L1 gene of an HPV-6 deletion mutant, Apr. 13, 1999 [online], [retrieved on May 9, 2010], retrieved from the Internet: <URL: //www.ncbi.nlm.nih.gov/nuccore/4039082>.*
Tyagi et al. Molecular Beacons: Probes that Fluoresce upon Hybridization. Nature Biotechnology (1996) 14: 303-308.*
Ramachandran et al. Target discrimination by surface-immobilized molecular beacons designed to detect Francisella tularensis. Biosensors and Bioelectronics (2004) 19: 727-736.*
GenBank Accession No. AF335603.1 for the L1 gene of an HPV-11 isolate, Mar. 20, 2001 [online], [retreived on May 10, 2010], retrieved from the Internet: <URL: //www.ncbi.nlm.nih.gov/nuccore/13384100>.*
Szemes et al. Design of molecular beacons for AmpliDet RNA assay : Characterization of binding stability and probe specificity. Analytical Biochemistry (2003) 315: 189-201.*
Coutlee et al., "*Use of PGMY Primers in L1 Consensus PCR Improves Detection of Human Papillomavirus DNA in Genital Samples,*" 2002, pp. 902-907, Journal of Clinical Microbiology, V. 40, No. 3.
Deng et al., "*Two-dimensional micro-bubble actuator array to enhance the efficiency of molecular beacon based DNA microbiosensors,*" 2006, pp. 143-1450, Biosensors and Bioelectronics 21.
De Villiers, "*Heterogeneity of the Human Papillomavirus Group,*" 1989, pp. 4898-4903, Journal of Virology, V. 63, No. 11.
El Hajj et al., "*Detection of Rifampin Resistance in Mycobacterium tuberculosis in a Single Tube with Molecular Beacons,*" 2001, pp. 4131-4137, Journal of Clinical Microbiology, V. 39, No. 11.
Hsieh et al., "*An efficient algorithm for minimal primer set selection,*" 2003, pp. 285-286, Bioinformatics Applications Note, V. 19, No. 2.
Hubbard, "*Human Papillomavirus Testing Methods,*" 2003, pp. 940-945, Arch Pathol Lab Med, V. 127.

(Continued)

*Primary Examiner* — Young J Kim
*Assistant Examiner* — Angela Bertagna
(74) *Attorney, Agent, or Firm* — K&L Gates LLP

(57) ABSTRACT

A method for detecting pathogens, particularly organisms associated with sexually transmitted diseases, especially Human papilloma virus genotypes is described. The method involves the use of real-time PCR using specially designed probes. The probes, kits for carrying out the method, and methods for designing primers suitable for use in the method of the invention are also described.

2 Claims, No Drawings

OTHER PUBLICATIONS

Kleter et al., "Development and Clinical Evaluation of a Highly Sensitive PCR-Reverse Hybridization Line Probe Assay for Detection and Identification of Anogenital Human Papillomavirus," 1999, pp. 2508-2517, Journal of Clinical Microbiology, V. 37, No. 8.

Nilsson et al., "Real-time monitoring of rolling-circle amplification using a modified molecular beacon design," 2002, pp. 1-7, Nucleic Acids Research, V. 30, No. 14.

Ramachandran et al., "Capillary electrophoresis and fluorescence studies on molecular beacon-based variable length oligonucleotide target discrimination," 2003, pp. 70-77, Electrophoresis, V. 24.

Snijders et al., "The use of general primers in the polymerase chain reaction permits the detection of a broad spectrum of human papillomavirus genotypes," 1990, pp. 173-181, Journal of General Virology, V. 71.

Strohsahl et al., "Towards single-spot multianalyte molecular beacon biosensors," 2005, pp. 479-485, Talanta, V. 67.

Szuhai et al., "A Novel Strategy for Human Papillomavirus Detection and Genotyping with SybrGreen and Molecular Beacon Polymerase Chain Reaction," 2001, pp. 1651-1660, American Journal of Pathology, V. 159, No. 5.

Tsourkas et al., "Shedding light on health and disease using molecular beacons," 2003, pp. 372-384, Briefings in Functional Genomics and Proteomics, V. 1, No. 4.

Tsourkas et al., "Structure-function relationships of shared-stem and conventional molecular beacons," 2002, pp. 4208-4215, Nucleic Acids Research, V. 30, No. 19.

Tsourkas et al., "Hybridization kinetics and thermodynamics of molecular beacons," 2003, pp. 1319-1330, Nucleic Acids Research, V. 31, No. 4.

Vogelstein et al., "Digital PCR," 1999, pp. 9236-9241, Proc. Natl. Acad. Sci. USA, V. 96.

International Search Report from the International Searching Authority for International Application No. PCT/GB2006/004266, mailed Jun. 11, 2007, 13 pages.

Written Opinion of the International Searching Authority for International Application No. PCT/GB2006/004266, mailed Jun. 11, 2007, 15 pages.

European Search Report from the European Patent Office for European Application No. EP 06 80 8556.2, mailed Feb. 12, 2008, 5 pages.

* cited by examiner

SEQUENCE LISTING

<160> NUMBER OF SEQ ID NOS: 137

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
cgcaccaaca tattttatt                                                    19

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
cgcacaagca tctattatta                                                   20

<210> SEQ ID NO 3
<211> LENGTH: 19
<212> TYPE: DNA
<213> ORGANISM: Artificial
<220> FEATURE:
<223> OTHER INFORMATION: Primer

<400> SEQUENCE: 3
cgcacaagca tattttatc                                                    19

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
cgcaccagta tattttatca                                                   20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
cgcacaagca tttactatca                                                   20

<210> SEQ ID NO 6
<211> LENGTH: 19
<212> TYPE: DNA
<213> ORGANISM: Artificial
<220> FEATURE:
<223> OTHER INFORMATION: Primer

<400> SEQUENCE: 6
cgcaccaact acttttacc                                                    19

<210> SEQ ID NO 7
<211> LENGTH: 21
<212> TYPE: DNA

```
<213> ORGANISM: Artificial
<220> FEATURE:
<223> OTHER INFORMATION: Primer

<400> SEQUENCE: 7
cgtaccagta ttttctacca c                                            21

<210> SEQ ID NO 8
<211> LENGTH: 19
<212> TYPE: DNA
<213> ORGANISM: Artificial
<220> FEATURE:
<223> OTHER INFORMATION: Primer

<400> SEQUENCE: 8
cgcacaggca tatattact                                               19

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
cgcaccaaca tatattatca                                              20

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
cgtaccaacc tgtactatta tg                                           22

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
gcaccaactt attttaccat                                              20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
accaacctct tttattatgg                                              20

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
agcacaaata tatattatta tgg                                          23
```

```
<210> SEQ ID NO 14
<211> LENGTH: 18
<212> TYPE: DNA
<213> ORGANISM: Artificial
<220> FEATURE:
<223> OTHER INFORMATION: Primer

<400> SEQUENCE: 14
cgcaccggat atattact                                                     18

<210> SEQ ID NO 15
<211> LENGTH: 23
<212> TYPE: DNA
<213> ORGANISM: Artificial
<220> FEATURE:
<223> OTHER INFORMATION: Primer

<400> SEQUENCE: 15
cgcacaaata tttattatta tgc                                               23

<210> SEQ ID NO 16
<211> LENGTH: 19
<212> TYPE: DNA
<213> ORGANISM: Artificial
<220> FEATURE:
<223> OTHER INFORMATION: Primer

<400> SEQUENCE: 16
cggacgaatg tttattacc                                                    19

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
taccctaaat actctgtatt g                                                 21

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
taccctaaat accctatatt g                                                 21

<210> SEQ ID NO 19
<211> LENGTH: 21
<212> TYPE: DNA
<213> ORGANISM: Artificial
<220> FEATURE:
<223> OTHER INFORMATION: Primer

<400> SEQUENCE: 19
aattctaaaa actctgtact g                                                 21

<210> SEQ ID NO 20
<211> LENGTH: 21
<212> TYPE: DNA
<213> ORGANISM: Artificial
<220> FEATURE:
<223> OTHER INFORMATION: Primer
```

```
<400> SEQUENCE: 20
tactctaaat actctgtatt g                                          21

<210> SEQ ID NO 21
<211> LENGTH: 21
<212> TYPE: DNA
<213> ORGANISM: Artificial
<220> FEATURE:
<223> OTHER INFORMATION: Primer

<400> SEQUENCE: 21
taccttaaac actctatatt g                                          21

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
tattctaaat accctgtatt g                                          21

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
aactctaaat actctgtact g                                          21

<210> SEQ ID NO 24
<211> LENGTH: 21
<212> TYPE: DNA
<213> ORGANISM: Artificial
<220> FEATURE:
<223> OTHER INFORMATION: Primer

<400> SEQUENCE: 24
catcttaaaa accctatatt g                                          21

<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
aaccctaaac accctgtatt g                                          21

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
aacgcgaaaa accctatatt g                                          21

<210> SEQ ID NO 27
<211> LENGTH: 21
<212> TYPE: DNA
```

```
<213> ORGANISM: Artificial
<220> FEATURE:
<223> OTHER INFORMATION: Primer

<400> SEQUENCE: 27
taccctaaag accctatact g                                              21

<210> SEQ ID NO 28
<211> LENGTH: 21
<212> TYPE: DNA
<213> ORGANISM: Artificial
<220> FEATURE:
<223> OTHER INFORMATION: Primer

<400> SEQUENCE: 28
aactctaaat accctatact g                                              21

<210> SEQ ID NO 29
<211> LENGTH: 21
<212> TYPE: DNA
<213> ORGANISM: Artificial
<220> FEATURE:
<223> OTHER INFORMATION: Primer

<400> SEQUENCE: 29
aacgtgaaat acacgatatt g                                              21

<210> SEQ ID NO 30
<211> LENGTH: 21
<212> TYPE: DNA
<213> ORGANISM: Artificial
<220> FEATURE:
<223> OTHER INFORMATION: Primer

<400> SEQUENCE: 30
cacacggaac accctgtact g                                              21

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
caccctaaac accctatatt g                                              21

<210> SEQ ID NO 32
<211> LENGTH: 21
<212> TYPE: DNA
<213> ORGANISM: Artificial
<220> FEATURE:
<223> OTHER INFORMATION: Primer

<400> SEQUENCE: 32
aacccgaaac actcgatact g                                              21

<210> SEQ ID NO 33
<211> LENGTH: 23
<212> TYPE: DNA
<213> ORGANISM: Artificial
<220> FEATURE:
<223> OTHER INFORMATION: Probe

<400> SEQUENCE: 33
gggtcatcct tattttccca taa                                            23
```

-continued

```
<210> SEQ ID NO 34
<211> LENGTH: 25
<212> TYPE: DNA
<213> ORGANISM: Artificial
<220> FEATURE:
<223> OTHER INFORMATION: Probe

<400> SEQUENCE: 34
gggacatcca tattactcta tcaaa                                           25

<210> SEQ ID NO 35
<211> LENGTH: 27
<212> TYPE: DNA
<213> ORGANISM: Artificial
<220> FEATURE:
<223> OTHER INFORMATION: Probe

<400> SEQUENCE: 35 ggtcacccctt attactctat tacaaaa                                        27

<210> SEQ ID NO 36
<211> LENGTH: 21
<212> TYPE: DNA
<213> ORGANISM: Artificial
<220> FEATURE:
<223> OTHER INFORMATION: Probe

<400> SEQUENCE: 36
cacccatatt tcccccttaa a                                               21

<210> SEQ ID NO 37
<211> LENGTH: 20
<212> TYPE: DNA
<213> ORGANISM: Artificial
<220> FEATURE:
<223> OTHER INFORMATION: Probe

<400> SEQUENCE: 37
acgaccagca aacaagacac                                                 20

<210> SEQ ID NO 38
<211> LENGTH: 25
<212> TYPE: DNA
<213> ORGANISM: Artificial
<220> FEATURE:
<223> OTHER INFORMATION: Probe

<400> SEQUENCE: 38
caataacaaa atattagttc ctaaa                                           25

<210> SEQ ID NO 39
<211> LENGTH: 19
<212> TYPE: DNA
<213> ORGANISM: Artificial
<220> FEATURE:
<223> OTHER INFORMATION: Probe

<400> SEQUENCE: 39
tatcctgctt attgccacc                                                  19

<210> SEQ ID NO 40
<211> LENGTH: 21
<212> TYPE: DNA
<213> ORGANISM: Artificial
<220> FEATURE:
<223> OTHER INFORMATION: Probe
```

```
<400> SEQUENCE: 40 cataccdtaaa tctgacaatc c                                          21

<210> SEQ ID NO 41
<211> LENGTH: 24
<212> TYPE: DNA
<213> ORGANISM: Artificial
<220> FEATURE:
<223> OTHER INFORMATION: Probe

<400> SEQUENCE: 41 tttttagcg ttagtaggat tttt                                         24

<210> SEQ ID NO 42
<211> LENGTH: 25
<212> TYPE: DNA
<213> ORGANISM: Artificial
<220> FEATURE:
<223> OTHER INFORMATION: Probe

<400> SEQUENCE: 42
aaaacaagat tctaataaaa tagca                                       25

<210> SEQ ID NO 43
<211> LENGTH: 22
<212> TYPE: DNA
<213> ORGANISM: Artificial
<220> FEATURE:
<223> OTHER INFORMATION: Probe

<400> SEQUENCE: 43
ttaaagtggg tatgaatggt tg                                          22

<210> SEQ ID NO 44
<211> LENGTH: 19
<212> TYPE: DNA
<213> ORGANISM: Artificial
<220> FEATURE:
<223> OTHER INFORMATION: Probe

<400> SEQUENCE: 44
gctgttccta aggtatccg                                              19

<210> SEQ ID NO 45
<211> LENGTH: 19
<212> TYPE: DNA
<213> ORGANISM: Artificial
<220> FEATURE:
<223> OTHER INFORMATION: Probe

<400> SEQUENCE: 45
agcacgcgtt gaggtttta                                              19

<210> SEQ ID NO 46
<211> LENGTH: 21
<212> TYPE: DNA
<213> ORGANISM: Artificial
<220> FEATURE:
<223> OTHER INFORMATION: Probe

<400> SEQUENCE: 46
agttttagtt cccaaggtgt c                                           21

<210> SEQ ID NO 47
<211> LENGTH: 23
<212> TYPE: DNA
```

```
<213> ORGANISM: Artificial
<220> FEATURE:
<223> OTHER INFORMATION: Probe

<400> SEQUENCE: 47
ctgtgactaa ggacaatacc aaa                                            23

<210> SEQ ID NO 48
<211> LENGTH: 22
<212> TYPE: DNA
<213> ORGANISM: Artificial
<220> FEATURE:
<223> OTHER INFORMATION: Probe

<400> SEQUENCE: 48
ttccatcaaa agtcccaata ac                                             22

<210> SEQ ID NO 49
<211> LENGTH: 22
<212> TYPE: DNA
<213> ORGANISM: Artificial
<220> FEATURE:
<223> OTHER INFORMATION: Probe

<400> SEQUENCE: 49
aaaggtggta atggtagaca gg                                             22

<210> SEQ ID NO 50
<211> LENGTH: 23
<212> TYPE: DNA
<213> ORGANISM: Artificial
<220> FEATURE:
<223> OTHER INFORMATION: Probe

<400> SEQUENCE: 50
aatctggtac caaaacaaac atc                                            23

<210> SEQ ID NO 51
<211> LENGTH: 21
<212> TYPE: DNA
<213> ORGANISM: Artificial
<220> FEATURE:
<223> OTHER INFORMATION: Probe

<400> SEQUENCE: 51
ttaaggttcc tatgtctggg g                                              21

<210> SEQ ID NO 52
<211> LENGTH: 24
<212> TYPE: DNA
<213> ORGANISM: Artificial
<220> FEATURE:
<223> OTHER INFORMATION: Probe

<400> SEQUENCE: 52
tgacatagat ccccatagac agtt                                           24

<210> SEQ ID NO 53
<211> LENGTH: 135
<212> TYPE: DNA
<213> ORGANISM: Hpv2a

<400> SEQUENCE: 53
cggactaatg tgtattacca tggtggcagt tctaggcttc tcactgtggg tcatccatat    60
tactctataa agaagagtaa taataaggtg gctgtgccca aggtatctgg gtaccaatat   120
```

```
cgtgtatttc acgtg                                                     135
```

<210> SEQ ID NO 54
<211> LENGTH: 138
<212> TYPE: DNA
<213> ORGANISM: HPV3.

<400> SEQUENCE: 54

```
cgcaccaaca tttattatta tgcaggcagt tctcgcttgc tgaccgtggg tcatccttat    60
tttgctatcc ccaaatcttc taattccaag atggatattc ctaaggtgtc cgcctttcaa   120
tatagagtgt ttagggtg                                                  138
```

<210> SEQ ID NO 55
<211> LENGTH: 132
<212> TYPE: DNA
<213> ORGANISM: HPV6

<400> SEQUENCE: 55

```
cgcaccaaca tattttatca tgccagcagt tctagacttc ttgcagtggg tcatccttat    60
ttttccataa aacgggctaa caaaactgtt gtgccaaagg tgtcaggata tcaatacagg   120
gtatttaagg tg                                                        132
```

<210> SEQ ID NO 56
<211> LENGTH: 132
<212> TYPE: DNA
<213> ORGANISM: hpv11

<400> SEQUENCE: 56

```
cgcaccaaca tattttatca tgccagcagt tctagactcc ttgctgtggg acatccatat    60
tactctatca aaaaagttaa caaaacagtt gtaccaaagg tgtctggata tcaatataga   120
gtgtttaagg ta                                                        132
```

<210> SEQ ID NO 57
<211> LENGTH: 132
<212> TYPE: DNA
<213> ORGANISM: HPV13

<400> SEQUENCE: 57

```
cgtaccaaca tattttatca tgctagcagt tctagactac ttgcagtggg aaatccttat    60
tttcctatta agaaacaaaa caaaactgtt gtccctaagg tatctggtta tcagtttagg   120
gtatttaaag tt                                                        132
```

<210> SEQ ID NO 58
<211> LENGTH: 138
<212> TYPE: DNA
<213> ORGANISM: HPV16

<400> SEQUENCE: 58

```
cgcacaaaca tatattatca tgcaggaaca tccagactac ttgcagttgg acatccctat    60
tttcctatta aaaaacctaa caataacaaa atattagttc ctaaagtatc aggattacaa   120
tacagggtat ttagaata                                                  138
```

<210> SEQ ID NO 59
<211> LENGTH: 138
<212> TYPE: DNA
<213> ORGANISM: HPV18

<400> SEQUENCE: 59

```
cccacaagca tatttatca tgctggcagc tctagattat aactgttgg taatccatat    60 tttagggttc ctgcaggtgg tggcaataag caggatattc ctaaggtttc tgcataccaa   120
tatagagtat ttagggtg                                                138
```

<210> SEQ ID NO 60
<211> LENGTH: 135
<212> TYPE: DNA
<213> ORGANISM: HPV26

<400> SEQUENCE: 60

```
cgcaccggca tatattatta tgcgggcagc tctcgtttat aacattagg acatccatat    60 ttttccatac ctaaaactgg ccaaaaggcc gaaattccta aggtatctgc ctatcagtac   120
agggtattta gagtg                                                   135
```

<210> SEQ ID NO 61
<211> LENGTH: 138
<212> TYPE: DNA
<213> ORGANISM: HPV27

<400> SEQUENCE: 61

```
cggacgaatg tctattacca tggtggcagt tctaggctcc tcactgtcgg ccacccatat    60
tattctataa agaagggtag caataatagg ttggcagtgc ctaaggtgtc cggctaccaa   120
taccgtgtat ttcacgtt                                                138
```

<210> SEQ ID NO 62
<211> LENGTH: 138
<212> TYPE: DNA
<213> ORGANISM: HPV28

<400> SEQUENCE: 62

```
cgcaccaata tttattatta tgcaggcact tctcggttgc tgaccgtggg tcatccttat    60
tttcccattc ctaaatcatc cactaacaaa gcagatgtgc ccaaagtgtc cgcctttcag   120
tatagggtat tccgggtg                                                138
```

<210> SEQ ID NO 63
<211> LENGTH: 138
<212> TYPE: DNA
<213> ORGANISM: HPV29

<400> SEQUENCE: 63

```
cgcacaaata tttattatta tgcaggcagt tctcgcctgc tcactgtggg tcatccacat    60
tattcaattc ccaaatcctc tggtaataag gtagatgtgc ctaaggtgtc tgcatttcag   120
tacagggttt tccgtgtg                                                138
```

<210> SEQ ID NO 64
<211> LENGTH: 138
<212> TYPE: DNA
<213> ORGANISM: HPV30

<400> SEQUENCE: 64

```
cgcaccaata tatttatca tgcaggcagc tcacgtttgc ttgctgttgg acatccatat    60 tattctatt ctaaggctgg taattccaaa acagatgttc ccaaggtgtc tgcatttcag   120
tatagggtct ttagggtc                                                138
```

<210> SEQ ID NO 65
<211> LENGTH: 141
<212> TYPE: DNA

```
<213> ORGANISM: HPV31

<400> SEQUENCE: 65
cgaaccaaca tatattatca cgcaggcagt gctaggctgc ttacagtagg ccatccatat    60
tattccatac ctaaatctga caatcctaaa aaaatagttg taccaaaggt gtcaggatta   120
caatataggg tatttagggt t                                              141

<210> SEQ ID NO 66
<211> LENGTH: 140
<212> TYPE: DNA
<213> ORGANISM: HPV33

<400> SEQUENCE: 66
cgcacaagca tttattatta tgctggtagt tccagacttc ttgctgttgg ccatccatat    60
ttttctatta aaatcctact aacgctaaaa aattattggt acccaaagta tcaggcttgc   120
aatatagggt ttttagggtc                                                140

<210> SEQ ID NO 67
<211> LENGTH: 141
<212> TYPE: DNA
<213> ORGANISM: HPV34

<400> SEQUENCE: 67
cgcacaaata tatattatta tgcaggtagt acacgcttgc tggcagtagg acatccctat    60
tatcctataa aggatactaa tgggaaacgt aagattgctg tacctaaagt ttcaggtttg   120
caatacaggg tatttagaat a                                              141

<210> SEQ ID NO 68
<211> LENGTH: 137
<212> TYPE: DNA
<213> ORGANISM: HPV35

<400> SEQUENCE: 68
cgcacaaaca tctactatca tgcaggcagt tctaggctat tagctgtggg tcacccatac    60
tatgctatta aaaaacaaga ttctaataaa atagcagtac ccaaggtatc tggtttgcaa   120
tacagagtat ttagagt                                                   137

<210> SEQ ID NO 69
<211> LENGTH: 138
<212> TYPE: DNA
<213> ORGANISM: HPV39

<400> SEQUENCE: 69
cgcacaggca tatattatta tgctggcagc tctagattat taacagtagg acatccatat    60
tttaaagtgg gtatgaatgg tggtcgcaag caggacattc caaaggtgtc tgcatatcaa   120
tatagggtat ttcgcgtg                                                  138

<210> SEQ ID NO 70
<211> LENGTH: 135
<212> TYPE: DNA
<213> ORGANISM: HPV40

<400> SEQUENCE: 70
cgcaccagtt tatattatca tgctggtagt gccaggttac tgactatagg acatccatac    60
tttgagttaa aaaacccaa tggtgacatt tcagtgccta aggtttctgg acatcaatac   120
agggtattta gggta                                                     135
```

```
<210> SEQ ID NO 71
<211> LENGTH: 135
<212> TYPE: DNA
<213> ORGANISM: HPV42

<400> SEQUENCE: 71
cgcaccaact actttttacca tgccagcagt tctaggctat tggttgttgg tcacccttat      60
tactctatta caaaaaggcc aaataagaca tctatcccca aagtgtctgg tttacagtac     120
agagtattta gagtt                                                      135

<210> SEQ ID NO 72
<211> LENGTH: 135
<212> TYPE: DNA
<213> ORGANISM: HPV43

<400> SEQUENCE: 72
cgcaccaact tattttatta tgctggcagt tcacgtttgc ttgcagtggg tcacccatat      60 ttcccccctta aaaattcctc tggtaaaata actgtaccta aggtttctgg ttatcaatac    120
agagtattta gagtt                                                      135

<210> SEQ ID NO 73
<211> LENGTH: 132
<212> TYPE: DNA
<213> ORGANISM: HPV44

<400> SEQUENCE: 73
cgcaccaaca tatattacca tgctagcagt tctagacttc ttgctgtggg caacccttat      60
tttgccatac gaccagcaaa caagacactt gtgcctaagg tttcgggatt tcaatatagg    120 gttttttaaga tg                                                        132

<210> SEQ ID NO 74
<211> LENGTH: 141
<212> TYPE: DNA
<213> ORGANISM: HPV45

<400> SEQUENCE: 74
cgcacaagca tattttatca tgcaggcagt tcccgattat taactgtagg caatccatat      60
tttagggttg tacctaatgg tgcaggtaat aaacaggctg ttcctaaggt atccgcatat    120
cagtataggg tgtttagagt a                                              141

<210> SEQ ID NO 75
<211> LENGTH: 135
<212> TYPE: DNA
<213> ORGANISM: HPV51

<400> SEQUENCE: 75
cgcaccggca tatattacta tgcaggcagt tccagactaa taacattagg acatccctat      60
tttccaatac ctaaaacctc aacgcgtgct gctattccta agtatctgc atttcaatac     120 agggtattta gggta                                                      135

<210> SEQ ID NO 76
<211> LENGTH: 147
<212> TYPE: DNA
<213> ORGANISM: HPV52

<400> SEQUENCE: 76
cgcacaagca tctattatta tgcaggcagt tctcgattac taacagtagg acatccctat      60
```

```
tttctatta aaaacaccag tagtggtaat ggtaaaaaag ttttagttcc caaggtgtct    120
ggcctgcaat acagggtatt tagaatt                                      147

<210> SEQ ID NO 77
<211> LENGTH: 132
<212> TYPE: DNA
<213> ORGANISM: HPV53

<400> SEQUENCE: 77
cgcaccacta tattttatca tgctggaagc tctcgcttgc ttaccgtggg acatccttat    60
taccccattt ctaaatctgg taaagcagac atccctaagg tgtctgcatt tcagtatagg   120
gtgtttagag ta                                                       132

<210> SEQ ID NO 78
<211> LENGTH: 135
<212> TYPE: DNA
<213> ORGANISM: HPV54

<400> SEQUENCE: 78
cgcacaagca tatactatca tgcaagcagc tctagattat tggctgttgg acatccatat    60
tttaaagtac aaaaaaccaa taataagcaa agtattccta aagtatcagg atatcaatat   120
agggtgttta gggtg                                                    135

<210> SEQ ID NO 79
<211> LENGTH: 132
<212> TYPE: DNA
<213> ORGANISM: HPV55

<400> SEQUENCE: 79
cgcaccaaca tagtttacca tgctagcagt tctagacttc ttgctgtagg caacccttat    60
tttgccatac gaccagcaaa caagacactt gtgcctaaag tttcaggatt tcaatatagg   120
gtttttaagg tg                                                       132

<210> SEQ ID NO 80
<211> LENGTH: 135
<212> TYPE: DNA
<213> ORGANISM: HPV56

<400> SEQUENCE: 80
cgcactagta tattttatca tgcaggcagt tcacgattgc ttgccgtagg acatccctat    60
tactctgtga ctaaggacaa taccaaaaca aacattccca agttagtgc atatcaatat    120 agggtattta gggta                                                    135

<210> SEQ ID NO 81
<211> LENGTH: 138
<212> TYPE: DNA
<213> ORGANISM: HPV57

<400> SEQUENCE: 81
cggacgaatg tttattatca tggtgggagc tctcggctcc tcacagtagg ccatccatat    60
tattctataa aaaaaagtgg caataataag gtgtctgtgc ccaaggtatc gggctaccag   120
taccgtgtgt tccatgtg                                                 138

<210> SEQ ID NO 82
<211> LENGTH: 141
<212> TYPE: DNA
<213> ORGANISM: HPV58
```

```
<400> SEQUENCE: 82
cgcacaagca tttattatta tgctggcagt tccagacttt tggctgttgg caatccatat    60
ttttccatca aaagtcccaa taacaataaa aaagtattag ttcccaaggt atcaggctta   120
cagtataggg tctttagggt g                                             141

<210> SEQ ID NO 83
<211> LENGTH: 138
<212> TYPE: DNA
<213> ORGANISM: HPV59

<400> SEQUENCE: 83
cgtaccagta ttttctacca cgcaggcagt tccagacttc ttacagttgg acatccatat    60
tttaaagtac ctaaaggtgg taatggtaga caggatgttc ctaaggtgtc tgcatatcaa   120
tacagagtat ttagggtt                                                 138

<210> SEQ ID NO 84
<211> LENGTH: 144
<212> TYPE: DNA
<213> ORGANISM: HPV61

<400> SEQUENCE: 84
cgcaccaact tattttatta tggtggcagt tcccgtctgc ttactgtagg acatccctat    60
tgtagtttgc agcttgatgg gctgcagggc aagaaaaaca ctatccccaa ggtgtctggc   120
tatcaatata gggtgtttag ggta                                          144

<210> SEQ ID NO 85
<211> LENGTH: 138
<212> TYPE: DNA
<213> ORGANISM: HPV62

<400> SEQUENCE: 85
cgcaccaacc ttttttatta tgggggcagc tcccgccttc ttactgtggg acatccatat    60
tgtactttac aggttggcca gggtaaacgg gccaccattc ctaaggtgtc tgggtatcag   120
tacagggtgt ttcgtgtg                                                 138

<210> SEQ ID NO 86
<211> LENGTH: 135
<212> TYPE: DNA
<213> ORGANISM: HPV66

<400> SEQUENCE: 86
cgtaccagta tattttatca tgcaggtagc tctaggttgc ttgctgttgg ccatccttat    60
tactctgttt ccaaatctgg taccaaaaca aacatcccta agttagtgc atatcagtat   120 agagtgttta gggta                                                    135

<210> SEQ ID NO 87
<211> LENGTH: 141
<212> TYPE: DNA
<213> ORGANISM: HPV67

<400> SEQUENCE: 87
cgcacaagca tttactatta cgctggtagc tccagacttt tagctgtagg ccatccttac    60
ttttccattc ctaatccctc caacactaaa aaggtgttag tgcccaaggt gtcaggtttg   120
cagtataggg tatttagggt t                                             141

<210> SEQ ID NO 88
```

```
<211> LENGTH: 138
<212> TYPE: DNA
<213> ORGANISM: HPV68

<400> SEQUENCE: 88
cgcactggca tgtattacta tgctggtaca tctaggttat taactgtagg ccatccatat      60
tttaaggttc ctatgtctgg gggccgcaag cagggcattc ctaaggtgtc tgcatatcaa     120
tacagagtgt ttagggtt                                                    138

<210> SEQ ID NO 89
<211> LENGTH: 134
<212> TYPE: DNA
<213> ORGANISM: HPV69

<400> SEQUENCE: 89
cgcaccggat atattactat gcaggcagct ctcgattatt aactttgggt catccctatt      60
ttccaattcc taaatctggt tcaacagcag aaattcctaa agtgtctgct taccaatata     120 gggttttttcg tgtt                                                      134

<210> SEQ ID NO 90
<211> LENGTH: 138
<212> TYPE: DNA
<213> ORGANISM: HPV70

<400> SEQUENCE: 90
cgtacaggca tatattatta tgctggaagc tctcgcttat taacagtagg gcatccttat      60
tttaaggtac ctgtaaatgg tggccgcaag caggaaatac ctaaggtgtc tgcatatcag     120
tatagggtat ttagggta                                                    138

<210> SEQ ID NO 91
<211> LENGTH: 141
<212> TYPE: DNA
<213> ORGANISM: HPV72

<400> SEQUENCE: 91
cgcaccaacc tctattatta tggtggcagt tctcgtctac taactgtagg acatccttac      60
tgtgccatac ctctcaacgg acagggcaaa aaaaacacca ttcctaaggt ttcggggtat     120
caatacaggg tgtttagagt a                                                141

<210> SEQ ID NO 92
<211> LENGTH: 138
<212> TYPE: DNA
<213> ORGANISM: HPV73

<400> SEQUENCE: 92
agaacaaata tatattatta tgcaggtagc acacgtttgt tggctgtggg acacccatat      60
tttcctatca aggattctca aaaacgtaaa accatagttc ctaaagtttc aggtttgcaa     120
tacagggtgt ttaggctt                                                    138

<210> SEQ ID NO 93
<211> LENGTH: 132
<212> TYPE: DNA
<213> ORGANISM: HPV74

<400> SEQUENCE: 93
cgcaccaaca tcttttatca tgctagcagt tctagactac ttgctgtagg aaatccctat      60
ttccctataa aacaggttaa caaaacagtt gttcctaaag tgtctggata tcaatttagg     120
```

```
gtgtttaagg tg                                                         132

<210> SEQ ID NO 94
<211> LENGTH: 141
<212> TYPE: DNA
<213> ORGANISM: HPV81

<400> SEQUENCE: 94
cgcaccaacc ttttttatta tgggggcagt tcccgccttc ttactgtagg gcatccatat     60
tgtacattaa ctattggtac ccaaggaaag cgttccacta ttcccaaggt gtctgggtat    120
cagtaccggg tgtttcgtgt g                                              141

<210> SEQ ID NO 95
<211> LENGTH: 135
<212> TYPE: DNA
<213> ORGANISM: HPV82

<400> SEQUENCE: 95
cgcaccggca tatattatta tgcaggcagt tccagactta ttaccttagg acatccatat     60
ttttcaatac ccaaaaccaa tacacgtgct gaaatatacta aggtatctgc ctttcagtat   120
agggtgttta gggta                                                     135

<210> SEQ ID NO 96
<211> LENGTH: 141
<212> TYPE: DNA
<213> ORGANISM: HPV83

<400> SEQUENCE: 96
cgcaccaacc tctttatta cggtggcagc tccagacttc ttaccgtagg acatccatat      60
tatcctgtac aggttaatgg tcaaggaaaa aaagccacta tccccaaggt ttctggctac    120
caatataggg tgtttcgcat t                                              141

<210> SEQ ID NO 97
<211> LENGTH: 150
<212> TYPE: DNA
<213> ORGANISM: HPV84

<400> SEQUENCE: 97
cgcaccaact tatttatta tggtggtagt tctcgcctgc ttactgtggg acatccatat      60
tattctgttc ctgtgtctac ccctgggcaa acaacaaaaa aggccactat ccccaaggtt   120
tctgggtatc aatacagggt gtttagggtc                                     150

<210> SEQ ID NO 98
<211> LENGTH: 138
<212> TYPE: DNA
<213> ORGANISM: HPV85

<400> SEQUENCE: 98
cgtaccagta cattttatca tgctggcagc tctaggcttc taaccgttgg acatccatac     60
tataaagtta cctcaaatgg aggccgcaag caagacattc ctaaagtgtc tgcctatcag   120
tatcgagtgt ttcgggtt                                                  138

<210> SEQ ID NO 99
<211> LENGTH: 153
<212> TYPE: DNA
<213> ORGANISM: HPV86

<400> SEQUENCE: 99
```

```
cgtaccaacc tatttttatta tggtggtagt tcccgcttgc ttactgtggg ccatccatat      60
tatcctgtta ctgtttcctc cagccctgga caaaacaaca aaaaggccaa tattcccaag     120
gtttcggggt atcaatacag ggttttttagg gtg                                 153
```

<210> SEQ ID NO 100
<211> LENGTH: 147
<212> TYPE: DNA
<213> ORGANISM: HPV87

<400> SEQUENCE: 100

```
cgcaccaact tatttttatta tggtggcagt tctcgcctgc ttactgtggg tcacccttac      60
tatccagtta ctgttaccac ccctggtcag aacaagaaat ccaatattcc aaaggtgtct     120
ggctatcagt acagggtgtt tcgggtg                                         147
```

<210> SEQ ID NO 101
<211> LENGTH: 141
<212> TYPE: DNA
<213> ORGANISM: HPV89

<400> SEQUENCE: 101

```
cgtaccaacc tgtactatta tggaggcagc tcccgcctta ttacagttgg ccacccttat      60
tatactgtac aggtcaatgg tgctaacaaa aaggccaaca tacctaaggt atcagggtat     120
caatacaggg tatttagggt a                                               141
```

<210> SEQ ID NO 102
<211> LENGTH: 141
<212> TYPE: DNA
<213> ORGANISM: HPV90

<400> SEQUENCE: 102

```
agaacaaaca tatattatta tgcaggcagt tcccgactgt taactgttgg ccatccttat      60
tttgctatca aaaagcaatc aggaaaaaac cctatagtgg ttcccaaggt gtctggatat     120
caatataggg tgtttagggt a                                               141
```

<210> SEQ ID NO 103
<211> LENGTH: 135
<212> TYPE: DNA
<213> ORGANISM: HPV91

<400> SEQUENCE: 103

```
cgcaccaact tattttacca tgctggcagt tcccgtttac tggctgtggg ccacccttttt     60 tttcctataa aaaataattc tggtaaagta attgttccta agtttcagg tcaccaatat      120 agggtgttta gagtt                                                      135
```

<210> SEQ ID NO 104
<211> LENGTH: 140
<212> TYPE: DNA
<213> ORGANISM: HPV-IC

<400> SEQUENCE: 104

```
cggacgaatg tttattacca gatagataga gatagatacc catatacaga taatgacata      60
gatccccata gacagtttat acagatcagt agcagttttt atatatgaga tgatgatagc     120
aatacagagt atttagggta                                                 140
```

<210> SEQ ID NO 105
<211> LENGTH: 25
<212> TYPE: DNA

```
<213> ORGANISM: Artificial
<220> FEATURE:
<223> OTHER INFORMATION: Probe

<400> SEQUENCE: 105
aaaacagttg taccaaaggt gtctg                                              25

<210> SEQ ID NO 106
<211> LENGTH: 20
<212> TYPE: DNA
<213> ORGANISM: Artificial
<220> FEATURE:
<223> OTHER INFORMATION: Probe

<400> SEQUENCE: 106
caaaaaggcc aaataagaca                                                    20

<210> SEQ ID NO 107
<211> LENGTH: 19
<212> TYPE: DNA
<213> ORGANISM: Artificial
<220> FEATURE:
<223> OTHER INFORMATION: Probe

<400> SEQUENCE: 107
cccccttaaa aattcctct                                                     19

<210> SEQ ID NO 108
<211> LENGTH: 20
<212> TYPE: DNA
<213> ORGANISM: Artificial
<220> FEATURE:
<223> OTHER INFORMATION: Probe

<400> SEQUENCE: 108
atacgaccag caaacaagac                                                    20

<210> SEQ ID NO 109
<211> LENGTH: 19
<212> TYPE: DNA
<213> ORGANISM: Artificial
<220> FEATURE:
<223> OTHER INFORMATION: Probe

<400> SEQUENCE: 109
tatgaatggt ggtcgcaag                                                     19

<210> SEQ ID NO 110
<211> LENGTH: 21
<212> TYPE: DNA
<213> ORGANISM: Artificial
<220> FEATURE:
<223> OTHER INFORMATION: Probe

<400> SEQUENCE: 110
aaaacaccag tagtgctaat g                                                  21

<210> SEQ ID NO 111
<211> LENGTH: 19
<212> TYPE: DNA
<213> ORGANISM: Artificial
<220> FEATURE:
<223> OTHER INFORMATION: Probe

<400> SEQUENCE: 111
ccaaaacaaa cattcccaa                                                     19
```

```
<210> SEQ ID NO 112
<211> LENGTH: 24
<212> TYPE: DNA
<213> ORGANISM: Artificial
<220> FEATURE:
<223> OTHER INFORMATION: Probe

<400> SEQUENCE: 112
atccatattt taaagtacct aaag                                              24

<210> SEQ ID NO 113
<211> LENGTH: 21
<212> TYPE: DNA
<213> ORGANISM: Artificial
<220> FEATURE:
<223> OTHER INFORMATION: Probe

<400> SEQUENCE: 113
caaatctggt accaaaacaa a                                                 21

<210> SEQ ID NO 114
<211> LENGTH: 24
<212> TYPE: DNA
<213> ORGANISM: Artificial
<220> FEATURE:
<223> OTHER INFORMATION: Probe

<400> SEQUENCE: 114
cccatagaca gtttatacag atca                                              24

<210> SEQ ID NO 115
<211> LENGTH: 19
<212> TYPE: DNA
<213> ORGANISM: Artificial
<220> FEATURE:
<223> OTHER INFORMATION: Probe

<400> SEQUENCE: 115
ataaaacggg ctaacaaaa                                                    19

<210> SEQ ID NO 116
<211> LENGTH: 20
<212> TYPE: DNA
<213> ORGANISM: Artificial
<220> FEATURE:
<223> OTHER INFORMATION: Probe

<400> SEQUENCE: 116
tacctaaaac tggccaaaag                                                   20

<210> SEQ ID NO 117
<211> LENGTH: 26
<212> TYPE: DNA
<213> ORGANISM: Artificial
<220> FEATURE:
<223> OTHER INFORMATION: Probe

<400> SEQUENCE: 117
attctaataa aatagcagta cccaag                                            26

<210> SEQ ID NO 118
<211> LENGTH: 31
<212> TYPE: DNA
<213> ORGANISM: Artificial Sequence
<220> FEATURE:
<223> OTHER INFORMATION: probe
```

-continued

<400> SEQUENCE: 118
cggcgggtca tccttatttt tccataagcc g                                    31

<210> SEQ ID NO 119
<211> LENGTH: 33
<212> TYPE: DNA
<213> ORGANISM: Artificial Sequence
<220> FEATURE:
<223> OTHER INFORMATION: probe

<400> SEQUENCE: 119
cggcgggaca tccatattac tctatcaaag ccg                                  33

<210> SEQ ID NO 120
<211> LENGTH: 35
<212> TYPE: DNA
<213> ORGANISM: Artificial Sequence
<220> FEATURE:
<223> OTHER INFORMATION: probe

<400> SEQUENCE: 120
cgcgggtcac ccttattact ctattacaaa acgcg                                35

<210> SEQ ID NO 121
<211> LENGTH: 29
<212> TYPE: DNA
<213> ORGANISM: Artificial Sequence
<220> FEATURE:
<223> OTHER INFORMATION: probe

<400> SEQUENCE: 121
ccggcaccca tatttccccc ttaaaccgg                                       29

<210> SEQ ID NO 122
<211> LENGTH: 28
<212> TYPE: DNA
<213> ORGANISM: Artificial Sequence
<220> FEATURE:
<223> OTHER INFORMATION: probe

<400> SEQUENCE: 122
ccggacgacc agcaaacaag acacccgg                                        28

<210> SEQ ID NO 123
<211> LENGTH: 33
<212> TYPE: DNA
<213> ORGANISM: Artificial Sequence
<220> FEATURE:
<223> OTHER INFORMATION: probe

<400> SEQUENCE: 123
cggccaataa caaaatatta gttcctaaag ccg                                  33

<210> SEQ ID NO 124
<211> LENGTH: 27
<212> TYPE: DNA
<213> ORGANISM: Artificial Sequence
<220> FEATURE:
<223> OTHER INFORMATION: probe

<400> SEQUENCE: 124
ccggtatcct gcttattgcc accccgg                                         27

<210> SEQ ID NO 125
<211> LENGTH: 29
<212> TYPE: DNA

```
<213> ORGANISM: Artificial Sequence
<220> FEATURE:
<223> OTHER INFORMATION: probe

<400> SEQUENCE: 125
cggccatacc taaatctgac aatccgccg                                29

<210> SEQ ID NO 126
<211> LENGTH: 32
<212> TYPE: DNA
<213> ORGANISM: Artificial Sequence
<220> FEATURE:
<223> OTHER INFORMATION: probe

<400> SEQUENCE: 126
gccgtttttt agcgttagta ggattttcg gc                             32

<210> SEQ ID NO 127
<211> LENGTH: 33
<212> TYPE: DNA
<213> ORGANISM: Artificial Sequence
<220> FEATURE:
<223> OTHER INFORMATION: probe

<400> SEQUENCE: 127
cggcaaaaca agattctaat aaaatagcag ccg                           33

<210> SEQ ID NO 128
<211> LENGTH: 30
<212> TYPE: DNA
<213> ORGANISM: Artificial Sequence
<220> FEATURE:
<223> OTHER INFORMATION: probe

<400> SEQUENCE: 128
cggcttaaag tgggtatgaa tggttggccg                               30

<210> SEQ ID NO 129
<211> LENGTH: 27
<212> TYPE: DNA
<213> ORGANISM: Artificial Sequence
<220> FEATURE:
<223> OTHER INFORMATION: probe

<400> SEQUENCE: 129
ccgggctgtt cctaaggtat ccgccgg                                  27

<210> SEQ ID NO 130
<211> LENGTH: 27
<212> TYPE: DNA
<213> ORGANISM: Artificial Sequence
<220> FEATURE:
<223> OTHER INFORMATION: probe

<400> SEQUENCE: 130
cggcagcacg cgttgaggtt ttagccg                                  27

<210> SEQ ID NO 131
<211> LENGTH: 29
<212> TYPE: DNA
<213> ORGANISM: Artificial Sequence
<220> FEATURE:
<223> OTHER INFORMATION: probe

<400> SEQUENCE: 131
ccggagtttt agttcccaag gtgtcccgg                                29
```

```
<210> SEQ ID NO 132
<211> LENGTH: 31
<212> TYPE: DNA
<213> ORGANISM: Artificial Sequence
<220> FEATURE:
<223> OTHER INFORMATION: probe

<400> SEQUENCE: 132
cccgctgtga ctaaggacaa taccaaacgg g                           31

<210> SEQ ID NO 133
<211> LENGTH: 30
<212> TYPE: DNA
<213> ORGANISM: Artificial Sequence
<220> FEATURE:
<223> OTHER INFORMATION: probe

<400> SEQUENCE: 133
cggcttccat caaaagtccc aataacgccg                             30

<210> SEQ ID NO 134
<211> LENGTH: 30
<212> TYPE: DNA
<213> ORGANISM: Artificial Sequence
<220> FEATURE:
<223> OTHER INFORMATION: probe

<400> SEQUENCE: 134
cggcaaaggt ggtaatggta gacagggccg                             30

<210> SEQ ID NO 135
<211> LENGTH: 31
<212> TYPE: DNA
<213> ORGANISM: Artificial Sequence
<220> FEATURE:
<223> OTHER INFORMATION: probe

<400> SEQUENCE: 135
cggcaatctg gtaccaaaac aaacatcgcc g                           31

<210> SEQ ID NO 136
<211> LENGTH: 29
<212> TYPE: DNA
<213> ORGANISM: Artificial Sequence
<220> FEATURE:
<223> OTHER INFORMATION: probe

<400> SEQUENCE: 136
cggcttaagg ttcctatgtc tgggggccg                              29

<210> SEQ ID NO 137
<211> LENGTH: 32
<212> TYPE: DNA
<213> ORGANISM: Artificial Sequence
<220> FEATURE:
<223> OTHER INFORMATION: probe

<400> SEQUENCE: 137
cggctgacat agatccccat agacagttgc cg                          32
```

METHOD FOR DETECTING PATHOGENS USING MOLECULAR BEACONS

CROSS REFERENCE TO RELATED APPLICATIONS

This application is the U.S. National Phase Application of International Patent Application Serial No. PCT/GB06/004266, filed Nov. 15, 2006, published under PCT Article 21(2) in English, which claims priority to and the benefit under 35 U.S.C. Section 119(e) of U.S. Provisional Patent Application Ser. No. 60/737,006, filed Nov. 15, 2005, and which claims priority to and the benefit under 35 U.S.C. Section 365 of Great Britain Patent Application Serial No. 0523250.9, filed Nov. 15, 2005, the entire disclosures of each of which are incorporated by reference herein.

This invention relates to diagnostics specifically for organisms associated with sexually transmitted diseases, and more particularly to detection of human papillomavirus (HPV) genotypes, particularly genital human papillomavirus genotypes.

Human Papillomavirus and its Significance

According to the World Health Organization (WHO), cervical cancer is the second most common cause of cancer death in women. The presence of HPV infection has been implicated in more than 99% of cervical cancers worldwide. As estimated, more than 500,000 women worldwide develop cervical cancer in every year, and more than 273,000 of the cases are fatal. Even with Pap screening programs, a significant number of women die from cervical cancer each year.

HPV infection is the most frequent sexually transmitted disease (STD) worldwide, and up to 60% of sexually active women will be infected by HPV in the genital tract once in their lifetime. Irrespective of HPV infection status, fewer than 1 in 10,000 women will develop invasive cervical cancer. The fact that most HPV-infected women do not develop cytological anomalies or cancer underlines the importance of factors modulating the progression of cervical disease to cancer in HPV-infected women. These factors may include the HPV genotype and molecular variant, the HPV viral load, persistence of HPV infection, co-infection with other STD agents, the immune status of the host and environmental factors such as smoking.

Papillomaviruses are small DNA viruses that infect mammalian epithelial cells, causing epithelial proliferative lesions which may be benign, e.g., fibropapillomas (warts), or which may be malignant. All papillomaviruses are similar in that the genome size, organization, open reading frames, and protein functions are shared. Many, but not all, genome regions are conserved among the various papillomaviruses.

Because of the close association between the papillomavirus life cycle and the differentiation state of the host cell, the details of the papillomavirus life cycle have not been completely elucidated. It is known that papillomaviruses infect host epithelial basal cells, where the viral genomes become established and are maintained as low copy-number episomes that replicate in coordination with host cell replication. As the infected cells differentiate into keratinocytes, viral DNA is amplified, the late genes are induced, and vegetative replication of the papillomavirus follows.

Papillomaviruses infect a wide variety of animals, including humans. The human papillomaviruses (HPV) (including Papillomaviridae family, Alpha-, Beta-, Gamma-, Delta-, Mupapillomavirus and unclassified Papillomaviridae genera) are common causes of sexually transmitted disease. Several types of HPV have been identified by DNA sequence data, and 96 HPV genotypes have been fully sequenced to date.

Genotyping of HPV is based on DNA sequences of the L1, E6, and E7 genes. A 10% difference in sequence with respect to previously established strains is sufficient to define a new type of virus.

The heterogeneity of the human papillomavirus group is generally described in deVilliers, 1989, J. Virology 63:4898-4903, which is incorporated herein by reference. The genomes of numerous HPV types have been sequenced and/or characterized.

HPVs are DNA tumour viruses whose genome is organized in three regions:

the early gene (E1 to E7), the late gene (L1 and L2) regions and the upper regulatory region (URR) or long control region (LCR). The URR possesses binding sites for many repressors and activators of transcription, suggesting that it may play a part in determining the range of hosts for specific HPV types. E1 and E2, meanwhile, encode proteins that are vital for extrachromosomal DNA replication and the completion of the viral life cycle. The E2 encodes two proteins: one, which inhibits transcription of the early region; and the other, which increases the transcription of the early region. A hallmark of HPV-associated cervical carcinoma is loss of the expression of the viral E2 proteins. Recently a new E2 protein, consisting of the product of the small E8 ORF with the part of the E2 protein, was described. This protein able to repress both viral replication and transcription, and is therefore believed to have a major role in viral latency.

The E4 protein is expressed in the later stages of infection when complete virions are being assembled, and is not known to have transforming properties; however it is considered to play an important role for the maturation and replication of the virus. The E4 protein also induces the collapse of the cytoplasmic cytokeratin network in human keratinocytes, a situation which may assist the release of virions from the infected cell.

The E5 open reading frame (ORF), meanwhile, is often deleted in cervical carcinoma cells, indicating that it might not be essential in maintaining the malignant transformation of the host cell. When present, E5 interacts with various transmembrane proteins like the receptors of the epidermal growth factor, platelet-derived growth factor β, and colony stimulating factor. A study using HPV 16-infected cells found the E5 protein to possess weak transforming activity.

In carcinogenesis, the E6 and E7 ORF are considered to play the most major roles. These two units encode for oncoproteins that allow replication of the virus and the immortalization and transformation of the cell that hosts the HPV DNA.

The late region units, L1 and L2 encode viral capsid proteins during the late stages of virion assembly. The protein encoded by L1 is highly conserved among different papilloma virus species. The minor capsid protein encoded by L2 has more sequence variations than that of the L1 protein.

HPV can infect the basal epithelial cells of the skin or inner tissue linings, and are, accordingly, categorized as either cutaneous or mucosal (anogenital) type.

The HPV DNA is usually extrachromosomal or episomal in benign cervical precursor lesions. However, in many cervical cancer cells as well as in cervical cancer cell lines and HPV-transformed human keratinocytes in vitro, the HPV DNA is integrated in the host genome.

Cancer tissues may contain both episomal and integrated HPV DNAs at the same time, although integration appears to occur more frequently in HPV 18-associated cervical cancer than in HPV 16-associated cervical cancer. Integrated HPV 16 is present in some premalignant lesions but is not always present in carcinomas. During HPV DNA integration, the viral genome usually breaks in the E1/E2 region. The break usually leads to the loss of the E1 and E2 regions. The loss of E2, which encodes proteins including one that inhibits the transcription of the E6 and E7 regions, has been known to result in uncontrolled and increased expression of E6 and E7 oncogenic proteins. Increased expression of E6 and E7, meanwhile, has been observed to lead to the malignant transformation of the host cells and to tumour formation. HPV viral integration into the host genomic DNA is associated with progression from polyclonal to monoclonal status in Cervical intraepithelial neoplasia (CIN), and these events play a fundamental role in the progression from low-grade to high-grade cervical neoplasia.

Patterns of DNA copy number imbalance (CNI) are characteristic of cervical squamous intraepithelial lesion (SIL) grade, human papillomavirus (HPV) status and postoperative recurrence. While some CNIs were seen at similar frequencies in HG-SIL (high grade SIL) and LG-SIL (low grade SIL), others, including gain on 1q, 3q and 16q, were found frequently in HG-SIL but not in LG-SIL. There were significantly more CNIs per case in HG-SILs showing loss of the HPV16 E2 gene and in HG-SILs that subsequently recurred. The data are consistent with sequential acquisition of CNIs in cervical SIL progression. Higher frequency of CNI in association with E2 gene loss supports in vitro evidence that high-risk HPV integration is associated with genomic instability.

Based on the available molecular, clinical and epidemiologic data, a subset of HPVs are unequivocally the etiologic agents for cervical cancers and their precursors. HPVs have been detected in about 90% of cervical adenocarcinomas and squamous cell carcinomas. The majority of HPV infections clear spontaneously, but persistent infection with HPV DNA has been found in metastases arising from cervical tumours. Nevertheless known high-risk (or oncogenic) HPV types are a significant risk factor for cervical cancer and are increasingly recognized for their role in other cancers. Virtually all cervical cancers (99%) contain the genes of high-risk HPVs, most commonly types 16, 18, 31, and 45. Other high-risk types include types 31, 33, 35, 39, 45, 51, 52, 56, 58, 59, 68, and 73. HPVs 31, 33, 35, 51 and 52 are sometimes regarded as "intermediate risks" because they are more common in mild or severe dysplastic lesions than in carcinomas. Among the high-risk strains, HPV 16 and 18 are the most closely associated with cervical carcinoma. The HPV16 DNA has been found in more than 50% of squamous cell carcinomas, while the HPV18 DNA has been found in more than 50% of adenocarcinomas. However, the great majority of anogenital HPVs have oncogenic potential.

HPV's interaction with host cells has two principal biological consequences:

a) All anogenital HPVs induce low grade squamous lesions, which are the morphologic correlate of a productive infection and the immortalisation phenotypes exerted by normal E6, E7 expression. The immortalisation is an inherent strategy of papillomaviruses to mobilise resources for the DNA replication and produce new progeny.

b) Rarely, HPVs induce a proliferative epithelial phenotype recognized as a high grade lesion and that is the proximate cytohistologic precursor of invasive cervical carcinoma, which might involve uncontrolled E6, E7 expression.

To date the clinical diseases, which are associated with HPV infections and the potential field of applications of HPV detection and typing methods include condyloma acuminatum, lichen sclerosus, squamosus cell hyperplasia, vulvar intraepithelial neoplasia, squamosus cell carcinoma, cervical intraepithelial neoplasia, cervical carcinoma, adenocarcinoma of the cervix, anal intraepithelial neoplasia, penile intraepithelial neoplasia, adenocarcinoma of the larynx, recurrent respiratory papillomatosis, and epidermodysplasias verruciformis. Recent evidence suggests that HPV may play a role in the development of prostate cancer in men as well.

Cervical cancer precursor lesions (intraepithelial lesions) or cytological abnormalities are tested using Papanicolaou Stain, known as the Pap Smear after the inventor George Papanicolaou. The technique involves smearing cervical scrapes on a glass slide, and staining the cells obtained from the ano genital tract with hematoxylin, a nuclear stain. The Pap smear, however, has a lack of repeatability and it is not sufficiently predictive of impending HPV-induced neoplasias. It has been shown that 25% of patients with advanced in situ carcinoma may present normal Pap smears a few years before diagnosis or the last negative cytology was uniformly positive in cervical cancer cases on re-examination. An increasingly prevalent problem is the occurrence of invasive cancer within 3 years of a negative Pap smear.

The current acceptable rate of false negatives (i.e., women who do have dysplasia according to an expert panel of pathologists looking at tissue biopsies rather than smear samples, but are not diagnosed that way during the routine smear screening) is roughly 5-10% but recent studies suggest that the actual rate may be much higher. Furthermore, in approximately 7-8% of cases, the Pap smear demonstrates atypical squamous cells of undetermined significance (AS-CUS). In an additional 20-30% of cases, the Pap smear may be insufficient for interpretation due to the presence of inflammatory cells. In the case of the cervix, flat warts (visualised by colposcopy) are suspected premalignant lesions. Histopathological progression of flat warts to carcinoma in situ and cervical cancer has been well described.

Intraepithelial lesions are common early events among women with incident HPV infection, and the interval between incident HPV-16 or HPV-18 infection and biopsy-confirmed CIN grade 2-3 appears to be relatively short. However studies have demonstrated that infection with high-risk HPV types is usually transient. Persistence of HPV infection substantially increases the risk of progression to high grade intraepithelial lesions and invasive disease.

The progression of the disease is variable and it is associated with the loss or persistence of HPV. Significant numbers of dysplastic lesions regress spontaneously, others fail to progress, while a few progress rapidly.

As a consequence of the preferential role of high-risk genotypes in cervical cancer and because of the different, consequential and characteristic type patterns for the other pathological conditions, both identification and typing of HPV is highly important. Additionally different types of high-risk HPV pose different risks to the affected individuals. For instance, HPV16 and HPV18 have been more consistently identified in higher grades of cervical dysplasia and carcinoma than other HPV types. HPV16 is also more prevalent in squamosus carcinoma cases, and HPV18 is more prevalent in adenocarcinoma cases.

HPV Diagnostics

From 1980, several viral genomes have been cloned and used as type-specific probes in the diagnosis of HPVs. Filter hybridization techniques have been used to detect HPV DNA in cervical scrapes collected in parallel with samples for routine cytology. HPV DNA probes have been used in different hybridization-based assays such as Southern and hybrid Dot/Southern assays to detect HPV DNA in clinically-derived tissue samples. Additionally, purified biopsy DNA and in situ hybridizations in preserved tissue specimens, that is, direct localization within the intact cell of those sequences complementary to the nucleic acid probes have been demonstrated.

A method for detecting HPV DNA types that utilizes a reverse-blotting procedure has been reported. The procedure involved forming a membrane to which genomic DNA from four different HPV types was bound and then hybridizing labelled DNA from a biological sample to the DNA bound to the membrane.

Numerous methods have been developed to detect human papillomavirus types using type-specific reaction, detecting one HPV type at a time. The Polymerase Chain reaction (PCR) has been used to amplify and detect the presence of HPV16 and HPV18 DNA, in particular to detect HPV16 in oral and cervical biopsies. A mixture of primers has been described for the specific amplification by PCR of HPV sequences in types 1a, 5, 6a, 8, 11, 16, 18, and 33. U.S. Pat. Nos. 4,683,195 and 4,683,202 disclose PCR and the use of PCR to detect the presence or absence of nucleic acid sequence in a sample.

U.S. Pat. No. 5,447,839, which is incorporated herein by reference, discloses a method for detection and typing of HPV. In this method, HPV DNA sequences in a sample are amplified by PCR using consensus primers which amplify both oncogenic and non-oncogenic HPV types. Thus, the presence of HPV in the sample is indicated by the formation of amplification products. HPV is then typed using type-specific DNA probes which hybridize with the amplified region of DNA. The type-specific hybridization probes disclosed in this patent are capable of identifying and distinguishing among five known oncogenic types of HPV, namely HPV-6, HPV-11, HPV-16, HPV-18 and HPV-33.

A variety of methods for detecting high-risk types of HPV have been devised. Many of these rely on the detection of unique sequences in the HPV genome. For example, DNA or RNA probes complementary to a portion of the genes of a particular high risk HPV strain have been reported in the art, as useful in screening for the presence of a particular strain of high-risk HPV in patient samples (U.S. Pat. No. 4,849,332, incorporated herein by reference). U.S. Pat. No. 5,705,627, incorporated herein by reference, reports use of PCR to amplify and detect HPV DNA using degenerate or mixed consensus primers, followed by typing using a mixture of genotype-specific DNA probes. Other examples of using consensus primers can be found in U.S. Pat. No. 5,364,758, and Kleter, B. et al., Am. J. of Pathology, vol. 153, No. 6, 1731-39 (1998). These references are also incorporated herein by reference.

There is a commercial method available, which is based on hybridisation and signal amplification. (Hybrid Capture II, Digene Corp.) However, this method reportedly has specificity problems due to the high sequence homology of some part of the HPV genomes.

The amplification based methods consist of a part responsible for sensitivity (amplification), which is separated from those parts responsible for specificity (detection by hybridisation). These techniques differ in the amplified genome section, the number of primers and the techniques of detection. The most often used amplification methods are GP5+-GP6+ (general primer—GP), MY9-MY11, PGMY, SPF, L1C and the type specific PCR reactions. The most often used detection techniques are sequence specific hybridization, restriction fragment length polymorphism (RFLP) and line probe assay (LiPA). Sometimes, but rarely, sequencing or other methods are applied. The analytical properties of the amplifications vary within a wide range and are characterised by the number genotypes, which can be amplified, the analytical sensitivity, specificity of the amplification/detection of genotypes and also by the differences of sensitivities between genotypes.

HPV Real-Time PCR

Human papillomavirus-16 (HPV-16) viral load could be a biomarker predictive of the presence of high-grade cervical lesions. Several real-time PCR assays have been developed to accurately measure HPV-16 viral load (HPV-16 L1, HPV-16 E6, and HPV-16 E6 PG). The methods are teaching us to perform HPV detection in real-time, but detecting only one genotype at a time.

Identification of HPV DNA in patients with juvenile-onset recurrent respiratory papillomatosis was carried out using SYBR® Green real-time PCR. The method is used to detect multiple human papillomavirus genotypes in a real-time PCR reaction. However the amplification method is different from that described in the present invention. The amplicon produced is longer (approx. 450 bp), than is accepted for a probe based real-time amplification method in the art. The preferred length is 150 bp or less. The detection method is aspecific and unable to differentiate the genotypes reliably, which necessitates subsequent viral typing using real-time PCR with type-specific primers for HPV types 6, 11, 16, 18, 31, and 33. This again detects the types of human papillomavirus in isolates, but only one genotype at a time.

Similarly others used a method where a single-tube nested reaction was used to detect human papillomavirus genotypes in a general manner. However, specific detection of groups were not described.

Another method was used to detect human papillomavirus DNA in sex partners again using a two-step approach to assess both the genotypes and viral load data. The method uses GP5+/6+ polymerase chain reaction (PCR), followed by reverse-line blot analysis. It was used for the detection of 45 HPV types in cervical and penile scrape samples. Viral loads were subsequently determined in scrape samples positive for HPV types 16, 18, 31, and 33 by a LightCycler-based real-time PCR assays. The GP5+/GP6+PCR generates an amplicon of 150 bp length, enabling the application of the real-time probe based methods However the method can not detect multiple genotypes or groups in one reaction.

A method for homogeneous real-time detection and quantification of nucleic acid amplification was devised using restriction enzyme digestion. In this homogeneous system detection is mediated by a primer containing a reporter and quencher moiety at its 5' terminus separated by a short section of DNA encoding a restriction enzyme recognition sequence. In the single stranded form, the signal from the fluorescent reporter is quenched due to fluorescence resonance energy transfer (FRET). However, as the primer becomes incorporated into a double stranded amplicon, a restriction enzyme present in the reaction cleaves the DNA linking the reporter and quencher, allowing unrestricted fluorescence of the reporter. This system was tested using a primer specific for the E6 gene of human papilloma virus (HPV) 16 combined with the cleavable energy transfer label and used to amplify HPV16 positive DNA. The method can not be used for the detection of multiple genotypes or groups.

A real-time PCR-based system for simultaneous quantification of human papillomavirus types associated with high risk of cervical cancer has also been described. A real-time PCR assay for the detection and quantification of HPV16, -18, -31, -33, -35, -39, -45, -52, -58, and -67 was developed. The assay is based on three parallel real-time PCRs from each patient sample: (i) reaction 1 detects and quantifies HPV16, -31, -18, and -45 (HPV18 and -45 were detected and quantified together using one probe) with three different fluorophores; (ii) reaction 2 detects and quantifies HPV33, -35, -39, -52, -58, and -67 (HPV33, -52, -58, and -67 were detected and quantified together), again with three different fluorophores and only three different probes were used; and (iii) reaction 3 detects and quantifies the amount of a human single copy gene (HMBS, *Homo sapiens* hydroxymethylbilane synthase; GenBank accession no. M95623.1). Reaction 1 includes a total of seven PCR primers and three probes, reaction 2 includes a total of seven PCR primers and three probes, and reaction 3 includes two PCR primers and a single probe. The method applies TaqMan hydrolysable real-time PCR probes. The use of only three probes in one reaction detecting a maximum of 6 genotypes in the same reaction is described. The method cannot be used as a general teaching to design reactions detecting multiple HPV genotypes, because the sequence identities between genotypes are limited. Extension of the reaction is restricted by using sequence identities between genotypes.

A method for the detection and quantitation of oncogenic human papillomavirus (HPV) was previously developed by using the fluorescent 5' exonuclease assay. The method is based on the amplification of a 180-bp fragment from the 3' part of the E1 open reading frame in a single PCR with type-specific probes for HPV types 16, 18, 31, 33, and 35. The probes can be used separately or in combinations of up to three probes per assay. The method was limited to three probes per assay.

A strategy for human papillomavirus detection and genotyping with SybrGreen and molecular beacon polymerase chain reaction has also been described. The assay, accomplishes general HPV detection by SybrGreen reporting of HPV-DNA amplicons, and genotyping of seven prevalent HPV types (HPV-6, -11, -16, -18, -31, -33, -45) by real-time molecular beacon PCR. The two step method uses three differently labelled molecular beacons in one PCR reaction.

Another method has also been described: a degenerate HPV self-probing fluorescent primer known as Scorpion and a mixture of Scorpions was used in conjunction with a tailed general primer. By utilizing a tailed primer, it was possible to introduce a consensus site that enables a single Scorpion to recognize many different HPV amplicons. This is a two-step procedure that can theoretically detect over 40 different HPV types. 10 Scorpion typing primers were used in this study (HPV6, 11, 16, 18, 31, 33, 39, 45, 51, 56). The primer sequence of each Scorpion is type specific and is located at the same sequence position as that of the GP6+ primer of Jacobs et al. The method teaches a general detection method to detect the presence of HPV and a type specific detection method used to type the positive samples. It does not solve the problem of screening with multiplexed probes, which leads to probe cross-reactivity. In fact the method avoids using of multiple probes in one reaction.

Real-time PCR based HPV detection methods using the real-time LightCycler™ and TaqMan™ assays have been compared to conventional GP5+/6+PCR/enzyme immunoassay (EIA) to assess the human papillomavirus load in cervical scrape specimens. Both real-time PCR assays determined the HPV16 load in scrape specimens similarly, but there was low agreement between these assays and the GP5+/6+PCR/EIA, suggesting that the latter method is not suited for quantifying HPV DNA. Also HPV6/11 and HPV16/18 DNA loads have been determined by real-time fluorogenic quantitative PCR detecting the two HPV gene types at a time.

Consensus Primer Design Methods

Primers and probes that are used to detect only one human papillomavirus nucleic acid molecule, e.g., a nucleic acid molecule encoding a portion of the L1, can be designed using, for example, a computer program such as OLIGO (Molecular Biology Insights Inc., Cascade, Colo.) or Primer3. Appropriate features of these oligonucleotides are well known for those skilled in the art.

There is extensive literature on the general principles of PCR primer design, which have led to a number of software applications, most notably Primer3 and various extensions. A fast dynamic programming formulation for testing primers for pair-wise compatibility has also been developed. The application of multiplex PCR has increased steadily over the past decade, requiring more sophisticated primer selection protocols. Different algorithms may favor particular objectives, or may be designed for particular technology platforms. In general, the problem of identifying primer pairs to maximize the multiplexing level of a single assay has been shown to be NP-complete. An approximation algorithm that eliminates 3' base complementarity while addressing product size constraints has been presented.

The method of the invention is related to the problem of designing multiplex PCR assays, particularly the design of consensus primers. The general approach of this problem is to design consensus primers to amplify numerous target with less primer pairs than the number of targets. Moreover the design would take into account the design rules of multiplex PCR assays as well, exemplified by a consensus herpesvirus.

A particular approach to identify distantly related gene sequences based on consensus-degenerate hybrid oligonucleotide primers (CODEHOPs) was developed. Short regions of proteins with high levels of conservation can be represented as ungapped blocks of multiply aligned protein sequences. CODEHOPs are derived from these conserved sequence blocks and are used in PCR to amplify the region between them. A CODEHOP PCR primer consists of a pool of primers each containing a different sequence in the 3' degenerate core region where each primer provides one of the possible codon combinations encoding a targeted 3-4 conserved amino acid motif within the sequence block. In addition, each primer in the pool has an identical 5' consensus clamp region derived from the most probable nucleotide at each position encoding the conserved amino acids flanking the targeted motif. Amplification initiates by annealing and extension of primers in the pool with the most similarity in the 3' degenerate core to the target template. Annealing is stabilized by the 5' consensus clamp which partially matches the target template. Once the primer is incorporated, it becomes the template for subsequent amplification cycles. Because all primers are identical in the 5' consensus clamp region, they all will anneal at high stringency during subsequent rounds of amplification. This method has been used in the field of virology as well. The approach is different from the method of the invention, where specific sequence blocks are used to achieve efficient amplification of related sequences. The Codehop program finds primers for amplifying unknown targets but works with protein sequence alignments instead of DNA sequences.

There are numerous methods dealing with the design of consensus/degenerate primers, but they generally use different algorhythms to solve basically the same problem: to identify the best-fit primer set for efficient amplification of the related target sequences. Cooperation between primers is not taken into account:

Another approach is the PriFi program (http://cgi-www.daimi.au.dk/cgi-chili/PriFi/main). This designs pairs of primers useful for PCR amplification of genomic DNA in species where prior sequence information is not available. The program works with an alignment of DNA sequences from phylogenetically related species and outputs a list of possibly degenerate primer pairs fulfilling a number of criteria, such that the primers have a high probability of amplifying orthologous sequences in other phylogenetically related species. However the program does not use the concept of cooperation between primers.

The Amplicon program for designing PCR primers on aligned groups of DNA sequences is a similar method. The most important application for Amplicon is the design of 'group-specific' PCR primer sets that amplify a DNA region from a given taxonomic group but do not amplify orthologous regions from other taxonomic groups. Again, the cooperation between primers was not taken into account.

The design of amplification reaction primers for detection by targeting numerous, related amplification targets has no straightforward rules in the literature. However it is generally accepted that the unforeseeable interactions between primers and the competition for amplification resources lower the sensitivity of the reaction and more primers means a larger probability of mispriming producing aspecific products competing further for the resources.

The potential role of HPV testing in cervical carcinoma screening is highly dependent on the existing infrastructure. For clinical settings in which an effective, well-organized, cytology based program is in place, the issue is whether HPV testing adds to the existing program and questions of cost effectiveness, quality control, and added value to current practice come to the fore. In contrast, for settings in which screening is nonexistent, or is ineffective because of poor-quality cytology or inherent limitations due to a high rate of inflammatory smears, the more basic questions of sensitivity, specificity, and simplicity of testing procedures become paramount.

The real-time PCR technology offers features which fulfil and even exceed the requirements in both scenarios described above. A recent study determined the amount of HPV DNA for some of the most frequent high-risk HPV types as determinants of progression to cervical malignancies (CIS). The range of copy numbers per cell does not differ between HPV types but the odds ratio for CIS in the percentile with highest viral load is substantially higher for HPV 16 (OR=36.9; 95% CI=8.9-153.2) than for HPV 31 (OR=3.2; 95% CI=1.1-9.1) or HPV 18/45 (OR=2.6; 95% CI=1.0-6.4). Therefore, HPV viral load may be predictive of future risk of cervical CIS at a stage when smears are negative for squamous abnormalities. The real-time technologies offer the premises to determine the viral load more exactly than the existing HPV detection methods. Real-time technology offers several advantages over the existing methods. However no real-time amplification and detection methods have been developed which can detect more than three human papillomavirus types in one reaction. Also, no method has been developed to detect clinically important groups of the virus, e.g. low-risk or high-risk human papillomaviruses in groups in one reaction.

An accurate self-sampled HPV test could have enormous implications. Such a test opens up the possibility of evaluating women who are otherwise unwilling or unable to submit to pelvic examinations. In underdeveloped areas this would offer an advantage over the current practice. In areas where organized screening is in place, self-sampling offers an additional approach for reaching women who refuse to have conventional screening and also may have a role in surveillance or the monitoring after the treatment of HPV-positive cytology-negative women, in which follow-up testing at short intervals is needed. The self-sampling approach with near-patient testing capabilities could improve the quality and accessibility of the screening programs.

A HPV test, which targets both the conventional and the primary screening market, should satisfy all of these needs. Real-time PCR technology is especially suitable to address these requirements technologically. The inherent simplicity of the technology helps to reduce infrastructure barriers and it is also cost-effective over other technologies. On the other side the real-time PCR technologies could boost the analytical sensitivity and more importantly the specificity of HPV detection, providing a more solid basis of the improvement of the clinical counterparts of these parameters. Internal control adds quality control capabilities to the system.

In the near-patient application of HPV detection the real-time technologies are the most feasible options. The near-patient testing would be the next frontier in primary screening and the real-time technologies are already attracted significant attention in this field in case of other pathogens and could provide added values in practice.

The increased sensitivity of real-time PCR compared to other methods, as well as the feature improvements provided by real-time PCR including sample containment and real-time detection of the amplified product indicate the feasibility of implementation of this technology for routine diagnosis of human papillomavirus infections in the clinical laboratory.

In the first aspect, the present invention provides a method of detecting the presence of at least one pathogen comprising contacting a nucleic acid obtained from a sample with a set comprising at least four probes wherein each of said probes comprises a sequence complementary to a sequence from pathogen flanked by four or five pairs of complementary bases, wherein said bases form a stem structure in the absence of hybridization to a nucleic acid from a pathogen, wherein said probe is labeled with a first interacting label and a second interacting label such that hybridizing of said probe to a nucleic acid from a pathogen causes a change in the signal detected.

As used herein, "nucleic acid" refers to DNA and RNA in its various forms such as mRNA, and hnRNA. The nucleic acid can be single stranded or double stranded.

As used herein a "pathogen" means a biological agent that disrupts the normal physiology of an animal, that causes or is associated with disease and illness. The pathogen may be a causative agent, i.e. infection of a patient with the pathogen produces the disease either alone, or in the presence of one more other cofactors.

Preferably the pathogen is an organism associated with a sexually transmitted disease. As used herein the term "organism associated with a sexually transmitted disease" refers to an organism that is present in patients suffering from the sexually transmitted disease. Examples of organisms associated with a sexually transmitted disease include *Chlamydia trachomatis* which is associated with chlamydia, *Neisseria gonorrhoeae* which is associated with Gonorrhoea, Herpes simplex virus (HSV) which is associated with genital herpes, Human pappillomavirus which is associated with genital warts and *Treponema pallidum* which is associated with Syphilis. The organism is preferably a virus, more preferably a human pappillomavirus (HHV). The method is preferably used to detect the presence of one or more HPV genotypes.

Although the method of the present invention relates to the detection of a pathogen, this method can be used to detect the presence or absence of any organism, particularly organisms which contain more than one sub-species, or related organisms. As used herein, "related organisms" refer to organisms which are from the same class, genus or species, and have a high level of genetic similarity, preferably at least 80% identity, more preferably 90%. The related organisms are preferably viruses, more preferably human papillomaviruses.

Each of the probes preferably has the general structure
3'-stem-F-HPV complementary sequence-F'-stem'-5'

F and F' are optional linking sequences which connect the complementary sequences to the flanking base pairs, stem and stem'. Stem and stem' are the sequences formed by the complementary base pairs which form a double-helix stem structure in the solution. These sequences are preferably palindromic. There are preferably 4 bases at each end of the probe. The bases making up the stem preferably comprise C-G pairs, preferably 1, 2, 3, 4 or 5 C-G pairs. The stem preferably has the sequence CGCG.

It was determined in our experiments that the four base pair-stem molecular beacons do not interact with each other causing unforeseeable false amplification signal over time in the absence of detectable target DNA, which seems to depend on the on-off rate of the stem structure. Occasionally five-base pair stem molecular beacons need to be used to optimise the reaction. Beacons with longer stems both in singleplex and multiplex detection exerted uncontrollable false amplification signals. Shorter stemmed beacons usually have too low melting temperatures to be useful in real-time amplification reaction.

The term "interacting label" as used herein refers to one of a pair of labels which cooperates with the other of the pair of the labels. This cooperation occurs when the labels are in close proximity, such as when the probes have a stem loop structure. When the probe hybridizes to a complementary nucleic acid, the cooperation between the labels is diminished, or removed completely as the distance between them is increased. The labels are attached to the probes at each end of the probe, preferably either on or adjacent to the complementary bases that form the stem loop structure. If is not important where the labels are attached provided that a change in signal can be detected when the probe changes from one conformation to the other i.e. stem loop to open. The change in signal can be an increase in signal when the probe is in the open position i.e. when it is hybridized to a complementary nucleic acid sequence, for example when one interacting label quenches the signal from the second interacting label. Alternatively the change in signal can be a decrease in signal when the probe is in the open position when it is hybridized to a complementary nucleic acid sequence, for example where the first interacting label causes a signal to be emitted from the second interacting signal.

In a preferred embodiment the interacting labels are a FRET donor and a corresponding FRET acceptor.

FRET technology (see, for example, U.S. Pat. Nos. 4,996,143, 5,565,322, 5,849,489, and 6,162,603) is based on the fact that when a donor and a corresponding acceptor fluorescent moiety are positioned within a certain distance of each other, energy transfer takes place between the two fluorescent moieties that can be visualized or otherwise detected and/or quantitated. As used herein, the FRET technology format utilizes molecular beacon technology to detect the presence or absence of a human papillomavirus. Molecular beacon technology uses a hybridization probe labelled with a donor fluorescent moiety and an acceptor fluorescent moiety. The fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e. the HPV genotype nucleic acid), the secondary structure of the probe is disrupted and the fluorescent moieties become separated from one another such that after excitation with light of a suitable wavelength, the emission of the first fluorescent moiety is different to that detected in the absence of a nucleic acid from a HPV genotype.

As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of the acceptor fluorescent moiety preferably should be at least 100 nm greater than the wavelength maximum of the excitation spectrum of the donor fluorescent moiety. Accordingly, efficient non-radiative energy transfer can be produced there between.

Fluorescent donor and acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, 4-acetamido-4'-isothiocyanatostilbene-2,2'-disulfonic acid derivatives, optionally substituted pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, Texas reds, ATTO dyes, EVO Dyes, DYO Dyes, Alexa dyes and BODIPY dyes.

Representative acceptor fluorescent moieties, depending upon the donor fluorescent moiety used, include LC™-RED 640 (LightCycler™-Red 640-N-hydroxysuccinimide ester), LC™-RED 705 (LightCycler™-Red 705-Phosphoramidite), cyanine dyes such as CY5 and CY5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

Preferably, the acceptor fluorescent moiety is a quencher. As used herein, a quencher is a moiety which decreases the fluorescence emitted by the fluorescent label. This includes complete and partial inhibition of the emission of the fluorescence. The degree of inhibition is not important as long as a change in fluorescence can be detected once the quencher is removed.

The quenching moiety is preferably selected from the group consisting of optionally substituted phenyls, naphthyls, anthracenyls, benzothiazoles, benzoxazoles, or benzimidazoles, pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, dabcyls, nitrotyrosines, malachite greens, Texas reds, dinitrobenzenes, ATTO dyes, EVO Dyes, DYO Dyes, Alexa dyes and BODIPY dyes.

The selection of suitable pairs of FRET donors and acceptors or quenchers is within the knowledge of the skilled person.

Generally, when the FRET is detected in an amount, which is statistically different from the amount of FRET in a sample lacking the human papillomavirus nucleic acid molecule the presence of a human papillomavirus infection in the individual is indicated. Hybridisation of the probe to the nucleic acid increases the distance between the donor and acceptor moiety, and thus the FRET interaction is reduced. The change in wavelength emission detected can be an increase in emission or emission at a different wavelength, such as when a quencher is used. Alternatively there can be a decrease in emission or emission at a different wavelength when a non-quenching donor acceptor is used.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range.

The donor and acceptor fluorescent moieties are preferably attached to the probe on the linking sequences. The donor and acceptor fluorescent moieties can be attached to the appropriate probe oligonucleotide via a linker arm. The length of each linker arm also is important, as the linker arms will affect the distance between the donor fluorescent moiety and the acceptor fluorescent moiety. The length of a linker arm for the purpose of the present invention is the distance in Angstroms (ANG) from the nucleotide base to the fluorescent moiety. In general, a linker arm is from about 10 to about 25 ANG. The linker arm may be of the kind described in WO 84/03285. WO 84/03285 also discloses methods for attaching linker arms to particular nucleotide bases, and also for attaching fluorescent moieties to a linker arm.

The probe must have a sufficient level of identity with the nucleic acid of the pathogen or organism associated with a sexually transmitted disease so that it can hybridize with nucleic acid from one or more pathogens or organisms associated with a sexually transmitted disease under suitable conditions. One single-stranded nucleic acid is said to hybridize to another if a duplex forms between them. This occurs when one nucleic acid contains a sequence that is the reverse or complement of the other (this same arrangement gives rise to the natural interaction between the sense and antisense strands of DNA in the genome and underlies the configuration of the double helix). Complete complementarity between the hybridizing regions is not required in order for a duplex to form; it is only necessary that the number of paired bases is sufficient to maintain the duplex under the hybridization conditions used. It is often desirable to have one or more mismatches between the sequence of the probe and that of the genome of the pathogen. This is necessary to prevent the formation of unwanted secondary structures within the probe. Thus in one preferred embodiment the sequence unique to the pathogen within the probe contains at least one mismatch with the genomic sequence of the pathogen. Suitable hybridization conditions are well known to the person skilled in the art. For example 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10-15 minutes each in the order listed above). Any or all of the washes can be repeated. Optimal conditions will vary and can be determined empirically by the skilled person.

The degree of identity between the probe and the pathogen's nucleic acid will vary depending on the function of the probe. For example the probe can be used to identify the presence of all sub-species of the pathogen, for example all HPV genotypes, in which case the probe will have a sequence which will hybridize to a sequence from a region of the nucleic acid which is highly conserved between all sub-species, such as HPV genotypes.

A probe can be used to detect the presence of pathogens, e.g. HPV genotypes, from a certain risk group, e.g. high risk or low risk genotypes or others. The sequence of the probe will be designed accordingly. For example a probe can be designed to detect high risk genotypes which can bind to types 31, 33, 35, 39, 45, 51, 52, 56, 58, 59, 68, and 73, but not nucleic acids from other genotypes. These are referred to as "risk group probes".

Alternatively each probe can have a sequence which has a high level of similarity to a variable region of a one specific genotype, so that it hybridises only to a nucleic acid from that genotype. Such probes are called "genotype specific". The members of the human papillomavirus type-specific probes can hybridize within defined genotype-specific regions, preferably those comprising SEQ ID. NOS: 53 to 103 on the amplified DNA. The HPV genotype specific probes preferably comprise a sequence selected from SEQ ID. NOS: 33 to 52 or SEQ II). Nos. 105 to 117. These sequences form all or part of the sequence unique to the pathogen.

The set of probes comprises at least four probes, preferably 5, 10, 15 or 20 different probes. The set of probes can comprise at least 10, at least 15 or at least 20 probes. The probes are carefully designed so that the sequence contained with the "loop" of the stem loop structure, not only hybridise with the desired sequence in the nucleic acid to be detected, but so they do not form secondary structures with sequences in the loops of other probes. Thus the sequences for the loop part of the probes are generally not just a sequence which is 100% complementary to the sequence in the genome to be detected. Preferably, the human papillomavirus type-specific probes can hybridize within defined type-specific regions, preferably those comprising SEQ ID. NOS: 53 to 103 or SEQ ID. Nos. 105 to 117. In one preferred embodiment each probes comprises a sequence selected from SEQ ID. NOS: 33 to 52 or SEQ ID. Nos. 105 to 117. In a particularly preferred embodiment the set of probes comprises:

```
                                        (SEQ ID NO: 118)
5'TET-CGGCGGGTCATCCTTATTTTTCCATAAGCCG-Dabcyl-3'

(SEQ ID NO: 119)
5'TET-CGGCGGGACATCCATATTACTCTATCAAAGCCG-Dabcyl-3'

(SEQ ID NO: 120)
5'TET-CGCGGGTCACCCTTATTACTCTATTACAAAACGCG-Dabcyl-3'

(SEQ ID NO: 121)
5'TET-CCGGCACCCATATTTCCCCCTTAAACCGG-Dabcyl-3'

(SEQ ID NO: 122)
5'TET-CCGGACGACCAGCAAACAAGACACCCGG-Dabcyl-3'

(SEQ ID NO: 123)
5'FAM-CGGCCAATAACAAAATATTAGTTCCTAAAGCCG-Dabcyl-3'

(SEQ ID NO: 124)
5'FAM-CCGGTATCCTGCTTATTGCCACCCCGG-Dabcyl-3'

(SEQ ID NO: 125)
5'FAM-CGGCCATACCTAAATCTGACAATCCGCCG-Dabcyl-3'

(SEQ ID NO: 126)
5'FAM-GCCGTTTTTTAGCGTTAGTAGGATTTTTCGGC-Dabcyl-3'

(SEQ ID NO: 127)
5'FAM-CGGCAAAACAAGATTCTAATAAAATAGCAGCCG-Dabcyl-3'

(SEQ ID NO: 128)
5'FAM-CGGCTTAAAGTGGGTATGAATGGTTGGCCG-Dabcyl-3'

(SEQ ID NO: 129)
5'FAM-CCGGGCTGTTCCTAAGGTATCCGCCGG-Dabcyl-3'

(SEQ ID NO: 130)
5'FAM-CGGCAGCACGCGTTGAGGTTTTAGCCG-Dabcyl-3'

(SEQ ID NO: 131)
5'FAM-CCGGAGTTTTAGTTCCCAAGGTGTCCCGG-Dabcyl-3'

(SEQ ID NO: 132)
5'FAM-CCCGCTGTGACTAAGGACAATACCAAACGGG-Dabcyl-3'

(SEQ ID NO: 133)
5'FAM-CGGCTTCCATCAAAAGTCCCAATAACGCCG-Dabcyl-3'

(SEQ ID NO: 134)
5'FAM-CGGCAAAGGTGGTAATGGTAGACAGGGCCG-Dabcyl-3'

(SEQ ID NO: 135)
5'FAM-CGGCAATCTGGTACCAAAACAAACATCGCCG-Dabcyl-3'

(SEQ ID NO: 136)
5'FAM-CGGCTTAAGGTTCCTATGTCTGGGGCCG-Dabcyl-3'
and
                                        (SEQ ID NO: 137)
5'(Texas Red)-TTTTTT-(fluorescein)-
CGGCTGACATAGATCCCCATAGACAGTTGCCG-Dabcyl-3'
```

The presence of pathogens from a particular risk group can be detected in two ways. Firstly "risk-group" probes can be used. Preferably the set of probes contains more than one type of risk group probe, wherein each type is differentially labelled. For example a high risk group probe can be distinguished from a low risk probe. Therefore the presence of a pathogen, such as HPV, from either risk group can be detected. Alternatively the set of probes can comprise genotype specific probes, wherein all the probes for genotypes from a certain risk group, e.g. high risk genotypes are all labelled with the same interacting labels. Thus the identity of the specific genotypes present can not be determined, but the presence of a genotype from a certain group can be confirmed.

In a preferred embodiment the method further comprises determining the melting temperature of the double stranded nucleic acid molecule formed by one of said probes and complementary nucleic acid obtained from said sample. As each of the probes has a certain nucleic acid sequence, the melting temperature of the double stranded nucleic acid molecule formed by the probes and the complementary nucleic acid obtained from said sample is unique for each probe. Thus the specific pathogen or genotype present can be detected. For example a set of genotype specific probes for a certain risk group can be used to ascertain if any genotypes from that group are present. The melting temperature can then be determined to identify which specific genotypes are present.

The method of detecting HPV types individually can be performed after the method has been performed to detect human papillomavirus family, genera or groups or concurrent with the method to detect human papillomavirus.

If more than one probe is used, they can preferably be distinguished from one another, i.e. each probe emits a detectably different signal when excited at a certain wavelength. Thus is two probes are used, one will emit at a wavelength when it is hybridised to nucleic acid from the pathogen that can be distinguished from both the probes in solution (i.e. not hybridised to the nucleic acid from the pathogen such as the HPV genotype) and the other probe when it is hybridised to the nucleic acid from the pathogen. This allows the presence of both probes hybridised to the nucleic acid to be visualised at the same time. Alternatively the two probes are labelled with different interacting labels, for example FRET donors, which are excited at different wavelengths.

This can be achieved by using different combinations of interacting labels, such FRET donors and acceptors. The selection of suitable combinations of interacting labels is routine to the person skilled in the art.

The method preferably detects the presence of four or more pathogens or genotypes, utilising four or more probes. Preferably the probes are bound to a solid phase such that each type of probe is at a spatially defined location which is distinguishable from the other probe locations. This allows probes labelled with the same or similar interacting labels which produce a signal at the same or similar wavelengths to be used, whilst still providing a means for distinguishing the signal produced by each probe. Alternatively the probes can be labelled so that different signals are produced by each type of probe. The skilled person will understand that a range of possible solid supports are in common usage in the area of arrays and any of these "substrates" can be utilized in the production of arrays of probes of the present invention.

In one preferred embodiment there is provided a method for constructing a reaction for the detection targeting of numerous, related detection targets using at least four real-time molecular beacon probes in one reaction. The method includes the selection of probe binding sites, determining the sequence of probes which satisfy the usually applied criteria on probes (e.g. checking the probes against a computer program at full complementarity like Primer3) and adding bases, preferably four or five bases, to the sequence of probe, at both ends, rendering them to be complementary and capable to form double-stranded stems involving exactly the two very ends of the same oligonucleotides. These structures are generally called four-stem molecular beacons. Additionally the melting point of the probe sequence should be higher than the melting point of the stem structure, when measured at near equilibrium heating and cooling rates. The four base-stem molecular beacons are generally advantageous over other stem length having shorter on-off rates than the longer stems, and having higher melting temperature than the shorter stem molecular beacons.

Generally, the members of the probe mixtures hybridize to the amplification product within a certain defined type-specific region. The probes are typically labelled with a donor fluorescent moiety at one end and at other end they are typically labelled with a corresponding acceptor or quencher fluorescent moiety. In some embodiments the donor fluorescent moiety may contain a specific complex of fluorescent dyes, including so called harvester dyes, to shift the wavelength of the emission of the probe to provide an unique fluorescent signal for detection. The method further includes detecting the presence, absence or change in fluorescent resonance energy transfer (FRET) between the donor fluorescent moiety and the acceptor or quencher fluorescent moiety. The presence of or change in FRET is indicative of the presence of human papillomavirus in the biological sample, while the absence of FRET is indicative of the absence of human papillomavirus in the biological sample.

Generally, the nucleic acid is hybridized with the probe and excited at a wavelength absorbed by the donor fluorescent moiety. The presence or absence of the bound probe is detected by visualizing and/or measuring the wavelength emitted by the acceptor or quencher fluorescent moiety. Alternatively it can be detected by quantitating the FRET.

In one preferred embodiment the nucleic acid obtained from a sample is amplified prior to being contacted with said set of probes. Preferably the amplification is carried out using the polymerase chain reaction (PCR). The amplification reaction may be PCR (see for example U.S. Pat. Nos. 4,683,195 and 4,683,202, and Innis et al, editors, PCR Protocols, (Academic Press, New York, 1989; Sambrook et al, Molecular Cloning, Second Edition, (Cold Spring Harbour Laboratory, New York 1989)). PCR will can also be used when RNA has been isolated and converted, preferably by reverse transcription, to cDNA. Preferably, PCR is carried out using Taq DNA polymerase, e.g. Amplitaq™ (Perkin-Elmer, Norwalk, Conn.). Taq polymerase can also be obtained from MBI Fermentas, Perkin Elmer, Boehringer Mannheim and Beckman Instruments. An equivalent, preferably thermostable, DNA polymerase may also be used in the method of the present invention, such as Tfl (*Thermus flavus*) polymerase (Gut et al, *Virol. Methods* 77(1): 37-46 (1999)).

Alternatively, the amplification reaction may be RT-PCR (Yajima et al, *Clin. Chem.*, 44(12): 2441-2445 (1998); Martell et al, *J. Clin. Microbiol.*, 37(2): 327-332 (1999); Gut et al, *Virol. Methods* 77(1): 37-46 (1999); Predhomme et al, *Leukemia*, 13(6): 957-964 (1999)), in which RNA is reverse transcribed into cDNA which is then subjected to PCR amplification.

As is well-known, PCR involves the extraction and denaturation (preferably by heat) of a sample of DNA (or RNA). A molar excess of oligonucleotide primers is added, along with a polymerase, which may be heat-stable, and dNTPs for forming the amplified sequence. The oligonucleotide primers are designed to hybridise to opposite ends of the sequence desired for amplification. In the first round of amplification, the polymerase replicates the DNA to produce two "long products," which begin with the respective primers. The total DNA, which includes the two long products and the two original strands, is then denatured and a second round of polymerisation is carried out (for example, by lowering the temperature). The result of the second round is the two original strands, the two long products from the first round, two new long products (produced from the original strands), and two "short products" produced from the long products. These short products have the sequence of the target sequence (sense or antisense) with a primer at each end. For each additional amplification round, the number of short products grows exponentially, each round producing two additional long products and a number of short products equal to the sum of the long and short products remaining at the end of the previous round.

Oligonucleotide primers can be synthesised by a number of approaches, e.g. Ozaki et al, *Nuc. Acids Res.* 20: 5205-5214 (1992); Agrawal et al, *Nuc. Acids Res.* 18: 5419-5423 (1990) or the like. Conveniently, the oligonucleotide probes are synthesised on an automated DNA synthesiser, e.g. an Applied Biosystems, Inc, Foster City, Calif. model 392 or 394 DNA/RNA synthesiser using standard chemistries such as phosphoramidite chemistry (Beaucage and Iyer, *Tetrahedron* 48: 2223-2311 (1992), U.S. Pat. Nos. 4,980,460, 4,725,677, 4,415,732, 4,458,066 and 4,973,679). Alternative chemistries, including non-natural backbone groups such as phosphorothioate and phosphoramidate, may also be employed, provided that the hybridisation efficiencies of the resulting oligonucleotides are not adversely affected. The precise length and sequence of the DNA primers will depend on the target polynucleotide to be amplified. Preferably, the length of the DNA primers is in the range 10 to 60 nucleotides and more preferably in the range 15 to 30 or 25 nucleotides.

Preferably, the production of the amplified nucleic acid is monitored continuously. As used herein "monitored continuously" means that the amount of amplified product is measured on a regular basis. For example a reading can be taken after the first amplification cycle, and thereafter after every one, two, or five cycles. Alternatively measurements of the amount of amplified product present can be taken after a certain time period, e.g. every one, two, five or ten seconds. This allows the process to be monitored in "real-time". The person skilled in the art would understand that the level of signal produced by the bound probes will fluctuate as the cycles passes through the various stages of annealing, amplification, and denaturing.

Conventional PCR methods in conjunction with FRET technology can be used to practice the methods of the invention. In one embodiment, a rapid thermocycler such as LIGHTCYCLER™ instrument is used. A detailed description of the LIGHTCYCLER™ System and real-time and on-line monitoring of PCR can be found on Roche's website. The following patent applications describe real-time PCR as used in the LIGHTCYCLER™ technology: WO 97/46707, WO 97/46714 and WO 97/46712. The LIGHTCYCLER™ instrument is a rapid thermocycler combined with a microvolume fluorimeter utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber. The instrument allows the PCR to be monitored in real-time and on-line. Furthermore, the cuvettes serve as an optical element for signal collection (similar to glass fiber optics), concentrating the signal at the tip of the cuvette. The effect is efficient illumination and fluorescent monitoring of microvolume samples. The carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorimeter, as part of the apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit in the instrument preferably includes three band-pass filters (530 nm, 640 nm, and 710 nm), providing six-colour detection and several fluorescence acquisition options. The present invention, however, is not limited by the configuration of a commercially available instrument. Data collection options include once per cycling step monitoring, fully continuous single-sample acquisition for melting curve analysis, continuous sampling (in which sampling frequency is dependent on sample number) and/or stepwise measurement of all samples after defined temperature interval. The thermocycler is preferably operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 msec. After each cycling step, a quantitative display of fluorescence vs. cycle number can be continually updated for all samples. The data generated can be stored for further analysis.

In a preferred embodiment the nucleic acid is amplified utilising at least one primer selected from Seq Id Nos 1 to 32, more preferably using a primer mixture comprising Seq Id Nos 1 to 32.

In one preferred embodiment the method utilises an artificial or natural internal control DNA, preferably by detecting signal or FRET emission at a different, distinguishable wavelength or regardless of the emission wavelengths used detecting, the emission changes at a spatially distinguishable location of solid phases bound probes.

The above-described methods can further include preventing amplification of contaminant nucleic acids from previous amplification reactions. Preventing such unwanted amplification can include performing the amplifying step in the presence of uracil and treating the biological sample with uracil-DNA glycosylase prior to a first amplification step. In addition, the cycling step can be performed on a separate control sample, to confirm proper amplification conditions. A control sample can include a portion of the human papillomavirus nucleic acid molecule. Alternatively, such a control sample can be amplified using a pair of control primers and hybridized using a pair of control probes. A control amplification product is produced if control template is present in the sample, and the control probes hybridize to the control amplification product.

The methods of the present invention are carried out on nucleic acids obtained from a biological sample. Representative biological samples include cervical scraping, biopsies, smear or paraffin tissue sections, other scrapings of anatomical sites where human papillomavirus infection takes place and urine. Preferably the sample is selected from bronchial aspirates, urine, prostata massate, ejaculatum, blood and cervical, vulvar, anal, genital, skin or laryngeal cytological samples, scrapings or biopsies.

In a second aspect the present invention provides a set of probes comprising least four probes wherein each of said probes comprises a sequence complementary to a sequence from a pathogen flanked by four pairs of complementary bases, wherein said bases form a stem structure in the absence of hybridization to a nucleic acid from a pathogen, wherein said probe is labeled with a first interacting label and a second interacting label such that hybridizing of said probe to a nucleic acid from said pathogen causes a change in the signal detected.

The preferred embodiments of the first aspect relating to the probes apply to the second aspect.

As described above, the sequences that form the "loop" part of the probe are selected so that they not only hybridize with the desired sequence in the target organism, but also so they do not form secondary structures with the loop regions of other probes. Thus in the third aspect the present invention provides a nucleic acid sequence comprising any one of SEQ ID Nos. 33 to 52 or SEQ ID Nos. 105-117. These nucleic acid sequences can be used in other methods to detect the presence of one or more HPV genotypes. Thus the present invention also provides the use of a nucleic acid of the invention for detecting the presence or absence of at least one HPV genotype. Preferably the nucleic acid is used in a method which continuously monitors the amplification of nucleic acid obtained from a sample.

Such methods include TAQMAN™ technology, the use of the sequences as part of a molecular scorpion, and other PCR based methods.

TAQMAN™ technology detects the presence or absence of an amplification product, and hence, the presence or absence of human papillomavirus. TAQMAN™ technology utilizes one single-stranded hybridization probe labelled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labelled hybridization probe binds to the target DNA and is degraded by the 5' to 3' exonuclease activity of the Taq Polymerase during the subsequent elongation phase. As a result, the excited fluorescent moiety and the second fluorescent moiety become spatially separated from one another. As a consequence, upon excitation of the first fluorescent moiety in the absence of the second fluorescent, the fluorescence emission from the first fluorescent moiety is detectably altered. For example if the second fluorescent moiety is a quencher, the fluorescence emission from the first fluorescent moiety increases and thus can be detected. By way of example, an ABI PRISM™ 7700 Sequence Detection System (Applied Biosystems, Foster City, Calif.) uses TAQMAN™ technology, and is suitable for performing the methods for detecting human papillomavirus. Information on PCR amplification and detection using an ABI PRISM™ 7700 system can be found on Applied Biosystems' website.

In a sixth aspect the present invention provides a method of identifying a minimal set of primers which amplify nucleic acid sequences from two or more related organisms comprising:
  (a) Identifying primer binding sites which have at least 30% identity between said organisms;
  (b) Designing a set of primers capable of initiating amplification at the primer sites identified in (a), wherein each of said primers has no more than 3 mismatches to a primer binding site in at least one of said organisms and wherein each of said primers differs from each of said primers by 4 or less nucleotides;
  (c) Determining the smallest number of primers required to detect the largest possible number of said organisms;
  (d) Determining the relative amount of each primer required in said primer set to ensure equal amplification of the nucleic acid sequences from all of said organisms.

As used herein, "related organisms" refer to organisms which are from the same class, genus or species, and have a high level of genetic similarity, preferably at least 80% identity, more preferably at least 90% identity. The related organisms are preferably viruses, more preferably human papillomaviruses. The primers preferably amplify the L1 region of human papillomaviruses.

The percent identity of two nucleic acid sequences is determined by aligning the sequences for optimal comparison purposes (e.g., gaps can be introduced in the first sequence for best alignment with the sequence) and comparing the nucleotides at corresponding positions. The "best alignment" is an alignment of two sequences which results in the highest percent identity. The percent identity is determined by the number of identical nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. The NBLAST and XBLAST programs of Altschul, et al. (1990) *J. Mol. Biol.* 215:403-410 have incorporated such an algorithm. BLAST nucleotide searches can be performed with the NBLAST program, score=100, wordlength=12 to obtain nucleotide sequences homologous to nucleic acid molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another example of a mathematical algorithm utilized for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) *Comput. Appl. Biosci.*, 10:3-5; and FASTA described in Pearson and Lipman (1988) *Proc. Natl. Acad. Sci.* 85:2444-8. Within FASTA, ktup is a control option that sets the sensitivity and speed of the search.

A minimal set of primers is a set of primers containing the smallest number of primers required to amplify nucleic acid sequences from as many related organisms as necessary. The set of primers can optionally contain a correction primer which is used to control priming differences between the primers at a particular primer binding site. The correction primers should have no more than three mismatches to the primer binding site where they are designed to act. The addition of correction primers helps to produce a level of sensitivity in detection which is at least two orders of magnitude or greater for all of the organisms intended to be detected e.g. all human papillomaviruses.

As used herein "mismatch" refers to when a base in a primer does not form a base-pair according to the Watson-Crick base pairing rules with a corresponding base in the primer binding site. A mismatch is formed where the two corresponding bases do not conform to the Watson-Crick criteria e.g. C-T, G-A. The mismatches are preferably within the half of the primer nearest the 5' end, more preferably forming the 3 nucleotides before the 5' end of primer.

Each of the primers in the primer set only differs from the each of the other primers in the set by four or less nucleotides.

Thus if the primers are all 15 nucleotides in length then 11 nucleotides in one primer are identical to 11 nucleotides in each of the other primers. The identical nucleotides are preferably not continuous.

In one preferred embodiment there is provided a method for constructing a highly complex multiplex reaction for human papillomavirus amplification. The method includes the selection of conserved primer binding sites (less than 70% variability) at an appropriate proximity. The primer binding sites should be located at a distance from each other to ensure that an amplicon of the appropriate size is produced. Preferably an amplicon of 30-160 nucleotides in length is produced, more preferably 40-120, 50-100, 60-90 or 70-80 nucleotides in length. Amplicons between 130 and 160 nucleotides in length are particularly preferred. The primers form part of the amplicon generated. The primers are preferably 10-30 nucleotides in length, more preferably 12-25, 15-22 or 18, 19, 20 or 21 nucleotides in length. The sequence of a complete set of primers where primers are satisfying the usually applied criteria for primers (e.g. checking the primers against a computer program at full complementarity like Primer3) is then determined, and the smallest possible number of primers are designed having only three mismatches, preferably on one end of the primer, more preferably the 5' end, to all of the related organisms, such as human papillomavirus types, which are intended to be amplified. Additionally the primers should bind to a nearly equal number of types with no more than three mismatches. Further amplification differences are controlled by changing the relative concentration of the primers. The resulting sensitivity of detection is preferably within at least two magnitudes for all related organisms, such as the human papillomavirus types, which are intended to be detected.

This is a significant achievement over the techniques in recent art, where sequential addition of the primers, and trial and error methods are followed. The devised method keeps the competition at a minimum. There are corrected priming efficiencies against all targets, resulting in highly equal amplification sensitivities. Additionally the probability of mispriming is reduced by keeping the primers preferably variable at the 5' end thereof.

The mixture of primers is capable of amplifying at least one human papillomavirus type L1 region, preferably comprising Seq ID Nos. 53 to 103. It preferably includes at least one forward primer from the group Seq Id Nos. 1 to 16 and at least one reverse primer from the group Seq ID Nos 17 to 32.

In a seventh aspect the present aspect provides a set of primers obtainable by the method of the sixth aspect comprising at least one primer selected from Seq. ID. Nos 1 to 32. Preferably it comprises at least one forward primer from the group Seq Id Nos. 1 to 16 and at least one reverse primer from the group Seq ID Nos 17 to 32. More preferably it comprises Seq. ID. Nos 1 to 32.

In a further aspect the present invention provides a kit for detecting one or more one or more pathogens comprising a set of probes as defined in the second aspect. The kit preferably further comprises a set of primers identified according to the method of the sixth aspect.

In addition, the invention provides a kit for detecting one or more pathogens comprising a set of primers identified according to the method of the sixth aspect.

Preferably the kits can be used to detect one or more organisms associated with a sexually transmitted disease, preferably HPV genotypes. Preferably the probes comprise a sequence selected from Seq ID nos. 17 to 33. The set of primers preferably comprise at least one sequence selected from Seq Id Nos 1 to 32, more preferably at least one selected from Seq ID No 1 to 16 and at least one selected from Seq Id 17-32. Most preferably the primer mixture comprises the primers of Seq Id Nos. 1-32.

Preferably the kits further comprise an internal control.

The kit can also include a package label or package insert having instructions thereon for using the mixture(s) of primers and pair(s) of probes to detect the presence or absence of human papillomavirus in a biological sample.

The kits can further comprise other components, such as reagents required for PCR. Such reagents include buffers, a suitable DNA polymerase, and dNTPs such as dATP, dCTP, dGTP and dTTP. The kit components can be presented in a number of vials or other containers. The reagents may be lyophilised for later reconstitution prior to use. Alternatively the components can be provided in suitable buffered solutions ready for use. Such solutions may contain suitable preservatives.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The invention is illustrated by the following non-limiting examples. Other features, objects, and advantages of the invention will be apparent from the drawings and detailed description, and from the claims.

EXAMPLE 1

Real-Time PCR Detection of High Risk and Low Risk HPV DNA

The total reaction-volume was 20 µl, including the following components: 2 µl (~0.2 pg) cloned HPV DNA, 18 µl polymerase buffer (final concentration: 90 mM TRIS-HCl (pH=8.0), 1 mM DTT, 50 mM KCl, 7 mM MgCl$_2$, 1% Tween-20 (SIGMA), 1% Ficoll, 1% PVP, 250 µM each dNTP (ATP, CTP, GTP, TTP) (Promega), 0.28 µM of each primers: SEQ. ID. NO: 1-32, 0.18 µM each of molecular beacons SEQ. ID. NO:33-52, and 7.5 U AmpliTaq Gold DNA polymerase (ROCHE)). The reaction was carried out in LightCycler 2.0 PCR thermal cycler, with the following parameters:
Step 1: 10 minutes at 95° C.;
Step 2: 5 minutes at 55° C.;
Step 3: Cycles 1-37: 30 seconds at 95° C., 60 seconds at 42° C.—single detection mode, and 30 seconds at 72° C.;

The high risk HPV genotypes were detected by molecular beacons SEQ. ID. NO:38-51. The fluorescent data were collected at 530 nm.

The low risk HPV genotypes were detected by molecular beacons SEQ. ID. NO:33-37. The fluorescent data were collected at 560 nm.

The reaction internal control was detected by molecular beacon SEQ. ID. NO:52. The fluorescent data was collected at 610 nm.

The following genotypes were successfully detected: low-risk (6, 11, 42, 43, 44/55), high-risk (16, 18, 31, 33, 35, 39, 45, 51, 52, 56, 58, 59, 66, 68) and internal control.

EXAMPLE 2

Real-Time PCR Detection of HPV16, HPV18 and HPV6, HPV11 HPV DNA

The total reaction-volume was 20 µl, including the following components: 2 µl (~0.2 pg) cloned HPV DNA, 18 µl polymerase buffer (final concentration: 90 mM TRIS-HCl (pH=8.0), 10 mM DTT, 50 mM KCl, 7 mM MgCl$_2$, 1% Tween-20 (SIGMA), 1% Ficoll, 1% PVP, 250 µM each dNTP (ATP, CTP, GTP, TTP) (Promega), 0.28 µM of each primers: SEQ. ID. NO: 1-32, 0.18 µM each of molecular beacons SEQ. ID. NO:33, 34, 38, 39, 52, and 7.5 U AmpliTaq Gold DNA polymerase (ROCHE)). The reaction was carried out in LightCycler 2.0 PCR thermal cycler, with the following parameters:
Step 1: 10 minutes at 95° C.;
Step 2: 5 minutes at 55° C.;
Step 3: Cycles 1-37: 30 seconds at 95° C., 60 seconds at 42° C.—single detection mode, and 30 seconds at 72° C.;

The HPV16 and HPV18 genotypes were detected by molecular beacons SEQ. ID. NO:38-39. The fluorescent data were collected at 530 nm.

The HPV6 and HPV11 genotypes were detected by molecular beacons SEQ. ID. NO:33-34. The fluorescent data were collected at 560 nm.

The reaction internal control was detected by molecular beacon SEQ. ID. NO:52. The fluorescent data was collected at 610 nm.

The following genotypes were successfully detected: low-risk (6, 11), high-risk (16, 18) and internal control.

APPENDIX 1

```
Forward primers:
SEQ. ID. NO: 1     KP-F/1      CGCACCAACATATTTTATT
SEQ. ID. NO: 2     KP-F/2      CGCACAAGCATCTATTATTA
SEQ. ID. NO: 3     KP-F/3      CGCACAAGCATATTTTATC
SEQ. ID. NO: 4     KP-F/4      CGCACCAGTATATTTTATCA
SEQ. ID. NO: 5     KP-F/5      CGCACAAGCATTTACTATCA
SEQ. ID. NO: 6     KP-F/6      CGCACCAACTACTTTTACC
SEQ. ID. NO: 7     KP-F/7      CGTACCAGTATTTTCTACCAC
SEQ. ID. NO: 8     KP-F/8      CGCACAGGCATATATTACT
SEQ. ID. NO: 9     KP-F/9      CGCACCAACATATATTATCA
SEQ. ID. NO: 10    KP-F/10     CGTACCAACCTGTACTATTATG
SEQ. ID. NO: 11    KP-F/11     GCACCAACTTATTTTACCAT
SEQ. ID. NO: 12    KP-F/12     ACCAACCTCTTTTATTATGG
SEQ. ID. NO: 13    KP-F/13     AGCACAAATATATATTATTATGG
SEQ. ID. NO: 14    KP-F/14     CGCACCGGATATATTACT
SEQ. ID. NO: 15    KP-F/15     CGCACAAATATTTATTATTATGC
SEQ. ID. NO: 16    KP-F/16     CGGACGAATGTTTATTACC
```

APPENDIX 1-continued

```
Reverse primers:
SEQ. ID. NO: 17    L1C2         TACCCTAAATACTCTGTATTG
SEQ. ID. NO: 18    L1R2         TACCCTAAATACCCTATATTG
SEQ. ID. NO: 19    R1           AATTCTAAAAACTCTGTACTG
SEQ. ID. NO: 20    R45          TACTCTAAATACTCTGTATTG
SEQ. ID. NO: 21    R11          TACCTTAAACACTCTATATTG
SEQ. ID. NO: 22    R16          TATTCTAAATACCCTGTATTG
SEQ. ID. NO: 23    R42          AACTCTAAATACTCTGTACTG
SEQ. ID. NO: 24    R44          CATCTTAAAAACCCTATATTG
SEQ. ID. NO: 25    R03          AACCCTAAACACCCTGTATTG
SEQ. ID. NO: 26    R04          AACGCGAAAAACCCTATATTG
SEQ. ID. NO: 27    R05          TACCCTAAAGACCCTATACTG
SEQ. ID. NO: 28    R06          AACTCTAAATACCCTATACTG
SEQ. ID. NO: 29    R07          AACGTGAAATACACGATATTG
SEQ. ID. NO: 30    R08          CACACGGAACACCCTGTACTG
SEQ. ID. NO: 31    R54          CACCCTAAACACCCTATATTG
SEQ. ID. NO: 32    R85          AACCCGAAACACTCGATACTG Probe sequences
SEQ.ID.NO: 33      HPV6B3:      GGGTCATCCTTATTTTTCCATAA
SEQ.ID.NO: 34      HPV11B2:     GGGACATCCATATTACTCTATCAAA
SEQ ID.NO: 35      HPV42B2:     GGTCACCCTTATTACTCTATTACAAAA
SEQ.ID.NO: 36      HPV43B2:     CACCCATATTTCCCCCTTAAA
SEQ.ID.NO: 37      HPV44/55B2:  ACGACCAGCAAACAAGACAC
SEQ.ID.NO: 38      HPV16B5:     CAATAACAAAATATTAGTTCCTAAA
SEQ.ID.NO: 39      HPV18B8:     TATCCTGCTTATTGCCACC
SEQ.ID.NO: 40      HPV31B5:     CATACCTAAATCTGACAATCC
SEQ.ID.NO: 41      HPV33B7:     TTTTTTAGCGTTAGTAGGATTTTT
SEQ.ID.NO: 42      HPV35B2:     AAAACAAGATTCTAATAAAATAGCA
SEQ.ID.NO: 43      HPV39B3:     TTAAAGTGGGTATGAATGGTTG
SEQ.ID.NO: 44      HPV45B3:     GCTGTTCCTAAGGTATCCG
SEQ.ID.NO: 45      HPV51B2:     AGCACGCGTTGAGGTTTTA
SEQ.ID.NO: 46      HPV52B2:     AGTTTTAGTTCCCAAGGTGTC
SEQ.ID.NO: 47      HPV56B2:     CTGTGACTAAGGACAATACCAAA
SEQ.ID.NO: 48      HPV58B2:     TTCCATCAAAAGTCCCAATAAC
SEQ.ID.NO: 49      HPV59B2:     AAAGGTGGTAATGGTAGACAGG
SEQ.ID.NO: 50      HPV66B2:     AATCTGGTACCAAAACAAACATC
SEQ.ID.NO: 51      HPV68B2:     TTAAGGTTCCTATGTCTGGGG
SEQ.ID.NO: 52      HPV-ICB2:    TGACATAGATCCCCATAGACAGTT SEQ.ID.NO: 53
>Hpv2a
cgga ctaatgtgta ttaccatggt ggcagttcta ggcttctcac tgtgggtcat
ccatattact ctataaagaa gagtaataat aaggtggctg tgcccaaggt
atctgggtac caatatcgtg tatttcacgt g SEQ.ID.NO: 54
>HPV3
cgc accaacattt attattatgc aggcagttct cgcttgctga ccgtgggtca
tccttatttt gctatcccca aatcttctaa ttccaagatg gatattccta
aggtgtccgc ctttcaatat agagtgttta gggtg SEQ.ID.NO: 55
>HPV6
cgcacca acatatttta tcatgccagc agttctagac ttcttgcagt
gggtcatcct tattttttcca taaaacgggc taacaaaact gttgtgccaa
aggtgtcagg atatcaatac agggtattta aggtg SEQ.ID.NO: 56
>hpv11
cgcacc aacatatttt atcatgccag cagttctaga ctccttgctg
tgggacatcc atattactct atcaaaaaag ttaacaaaac agttgtacca
aaggtgtctg gatatcaata tagagtgttt aaggta SEQ.ID.NO: 57
>HPV13
cgtac caacatatttt tatcatgcta gcagttctag actacttgca gtgggaaatc
cttatttttcc tattaagaaa caaaacaaaa ctgttgtccc taaggtatct
ggttatcagt ttagggtatt taaagtt SEQ.ID.NO: 58
>HPV16
cgcacaa acatatatta tcatgcagga acatccagac tacttgcagt
tggacatccc tattttccta ttaaaaaacc taacaataac aaaatattag
ttcctaaagt atcaggatta caatacaggg tatttagaat a
```

```
SEQ.ID.NO: 59
>HPV18
c ccacaagcat attttatcat gctggcagct ctagattatt aactgttggt
aatccatatt ttagggttcc tgcaggtggt ggcaataagc aggatattcc
taaggtttct gcataccaat atagagtatt tagggtg SEQ.ID.NO: 60
>HPV26
cgcacc ggcatatatt attatgcggg cagctctcgt ttattaacat
taggacatcc atattttcc atacctaaaa ctggccaaaa ggccgaaatt
cctaaggtat ctgcctatca gtacagggta tttagagtg SEQ.ID.NO: 61
>HPV27
cggacgaatg tctattacca tggtggcagt tctaggctcc tcactgtcgg
ccacccatat tattctataa agaagggtag caataatagg ttggcagtgc
ctaaggtgtc cggctaccaa taccgtgtat ttcacgtt SEQ.ID.NO: 62
>HPV28
cgca ccaatattta ttattatgca ggcacttctc ggttgctgac cgtgggtcat
ccttattttc ccattcctaa atcatccact aacaaagcag atgtgcccaa
agtgtccgcc tttcagtata gggtattccg ggtg SEQ.ID.NO: 63
>HPV29
c gcacaaatat ttattattat gcaggcagtt ctcgcctgct cactgtgggt
catccacatt attcaattcc caaatcctct ggtaataagg tagatgtgcc
taaggtgtct gcatttcagt acagggtttt ccgtgtg SEQ.ID.NO: 64
>HPV30
cg caccaatata ttttatcatg caggcagctc acgtttgctt gctgttggac
atccatatta ttctatttct aaggctggta attccaaaac agatgttccc
aaggtgtctg catttcagta tagggtcttt agggtc SEQ.ID.NO: 65
>HPV31
cg aaccaacata tattatcacg caggcagtgc taggctgctt acagtaggcc
atccatatta ttccatacct aaatctgaca atcctaaaaa aatagttgta
ccaaaggtgt caggattaca atatagggta tttaggggtt SEQ.ID.NO: 66
>HPV33
cgcacaagca tttattatta tgctggtagt tccagacttc ttgctgttgg
ccatccatat ttttctatta aaatcctac taacgctaaa aaattattgg
tacccaaagt atcaggcttg caatataggg ttttttagggt c SEQ.ID.NO: 67
>HPV34
cg cacaaatata tattattatg caggtagtac acgcttgctg gcagtaggac
atccctatta tcctataaag gatactaatg ggaaacgtaa gattgctgta
cctaaagttt caggtttgca atacagggta tttagaata SEQ.ID.NO: 68
>HPV35
cgcacaaaca tctactatca tgcaggcagt tctaggctat tagctgtggg
tcacccatac tatgctatta aaaaacaaga ttctaataaa atagcagtac
ccaaggtatc tggttttgcaa tacagagtat ttagagt SEQ.ID.NO: 69
>HPV39
c gcacaggcat atattattat gctggcagct ctagattatt aacagtagga
catccatatt ttaaagtggg tatgaatggt ggtcgcaagc aggacattcc
aaaggtgtct gcatatcaat atagggtatt tcgcgtg SEQ.ID.NO: 70
>HPV40
cgcaccag tttatattat catgctggta gtgccaggtt actgactata
ggacatccat actttgagtt aaaaaaaccc aatggtgaca tttcagtgcc
taaggtttct ggacatcaat acagggtatt tagggta SEQ.ID.NO: 71
>HPV42
cgcacca actactttta ccatgccagc agttctaggc tattggttgt
tggtcaccct tattactcta ttacaaaaag gccaaataag acatctatcc
ccaaagtgtc tggtttacag tacagagtat ttagagtt
```

APPENDIX 1-continued

```
SEQ.ID.NO: 72
>HPV43
cgcaccaact tattttatta tgctggcagt tcacgtttgc ttgcagtggg
tcacccatat ttccccctta aaaattcctc tggtaaaata actgtaccta
aggtttctgg ttatcaatac agagtattta gagtt SEQ.ID.NO: 73
>HPV44
cgc accaacatat attaccatgc tagcagttct agacttcttg ctgtgggcaa
cccttatttt gccatacgac cagcaaacaa gacacttgtg cctaaggttt
cgggatttca atatagggtt tttaagatg SEQ.ID.NO: 74
>HPV45
cgcaca agcatatttt atcatgcagg cagttcccga ttattaactg
taggcaatcc atattttagg gttgtaccta atggtgcagg taataaacag
gctgttccta aggtatccgc atatcagtat agggtgttta gagta SEQ.ID.NO: 75
>HPV51
cgc accggcatat attactatgc aggcagttcc agactaataa cattaggaca
tccctatttt ccaataccta aaacctcaac gcgtgctgct attcctaaag
tatctgcatt tcaatacagg gtatttaggg ta SEQ.ID.NO: 76
>HPV52
c gcacaagcat ctattattat gcaggcagtt ctcgattact aacagtagga
catccctatt tttctattaa aaacaccagt agtggtaatg gtaaaaaagt
tttagttccc aaggtgtctg gcctgcaata cagggtattt agaatt SEQ.ID.NO: 77
>HPV53
cgcaccact atattttatc atgctggaag ctctcgcttg cttaccgtgg
gacatcctta ttaccccatt tctaaatctg gtaaagcaga catccctaag
gtgtctgcat ttcagtatag ggtgtttaga gta SEQ.ID.NO: 78
>HPV54
cgcaca agcatatact atcatgcaag cagctctaga ttattggctg
ttggacatcc atattttaaa gtacaaaaaa ccaataataa gcaaagtatt
cctaaagtat caggatatca atatagggtg tttagggtg SEQ.ID.NO: 79
>HPV55
cgc accaacatag tttaccatgc tagcagttct agacttcttg ctgtaggcaa
cccttatttt gccatacgac cagcaaacaa gacacttgtg cctaaagttt
caggatttca atatagggtt tttaaggtg SEQ.ID.NO: 80
>HPV56
cgcacta gtatatttta tcatgcaggc agttcacgat tgcttgccgt
aggacatccc tattactctg tgactaagga caataccaaa acaaacattc
ccaaagttag tgcatatcaa tatagggtat ttagggta SEQ.ID.NO: 81
>HPV57
cgg acgaatgttt attatcatgg tgggagctct cggctcctca cagtaggcca
tccatattat tctataaaaa aaagtggcaa taataaggtc tctgtgccca
aggtatcggg ctaccagtac cgtgtgttcc atgtg SEQ.ID.NO: 82
>HPV58
c gcacaagcat ttattattat gctggcagtt ccagactttt ggctgttggc
aatccatatt tttccatcaa agtcccaat aacaataaaa aagtattagt
tcccaaggta tcaggcttac agtatagggt ctttagggtg SEQ.ID.NO: 83
>HPV59
cgtaccag tattttctac cacgcaggca gttccagact tcttacagtt
ggacatccat attttaaagt acctaaaggt ggtaatggta gacaggatgt
tcctaaggtg tctgcatatc aatacagagt atttagggtt SEQ.ID.NO: 84
>HPV61
cgcaccaact tattttatta tggtggcagt tcccgtctgc ttactgtagg
acatccctat tgtagtttgc agcttgatgg gctgcagggc aagaaaaaca
ctatccccaa ggtgtctggc tatcaatata gggtgtttag ggta
```

APPENDIX 1-continued

SEQ.ID.NO: 85
>HPV62
cgcacca accttttta ttatgggggc agctcccgcc ttcttactgt
gggacatcca tattgtactt tacaggttgg ccagggtaaa cgggccacca
ttcctaaggt gtctgggtat cagtacaggg tgtttcgtgt g SEQ.ID.NO: 86
>HPV66
cgtacca gtatatttta tcatgcaggt agctctaggt tgcttgctgt
tggccatcct tattactctg tttccaaatc tggtaccaaa acaaacatcc
ctaaagttag tgcatatcag tatagagtgt ttagggta SEQ.ID.NO: 87
>HPV67
cgcacaag catttactat tacgctggta gctccagact tttagctgta
ggccatcctt acttttccat tcctaatccc tccaacacta aaaaggtgtt
agtgcccaag gtgtcaggtt tgcagtatag ggtatttagg gtt SEQ.ID.NO: 88
>HPV68
cgcactggca tgtattacta tgctggtaca tctaggttat taactgtagg
ccatccatat tttaaggttc ctatgtctgg gggccgcaag cagggcattc
ctaaggtgtc tgcatatcaa tacagagtgt ttagggtt SEQ.ID.NO: 89
>HPV69
cgcac cggatatatt actatgcagg cagctctcga ttattaactt tgggtcatcc
ctattttcca attcctaaat ctggttcaac agcagaaatt cctaaagtgt
ctgcttacca atatagggtt tttcgtgtt SEQ.ID.NO: 90
>HPV70
cgta caggcatata ttattatgct ggaagctctc gcttattaac agtagggcat
ccttatttta aggtacctgt aaatggtggc cgcaagcagg aaatacctaa
ggtgtctgca tatcagtata gggtatttag ggta SEQ.ID.NO: 91
>HPV72
cgcacca acctctatta ttatggtggc agttctcgtc tactaactgt
aggacatcct tactgtgcca tacctctcaa cggacagggc aaaaaaaaca
ccattcctaa ggtttcgggg tatcaataca gggtgtttag agta SEQ.ID.NO: 92
>HPV73
agaaca aatatatatt attatgcagg tagcacacgt ttgttggctg
tgggacaccc atatttcct atcaaggatt ctcaaaaacg taaaaccata
gttcctaaag tttcaggttt gcaatacagg gtgtttaggc tt SEQ ID.NO: 93
>HPV74
cgcacc aacatctttt atcatgctag cagttctaga ctacttgctg
taggaaatcc ctatttccct ataaaacagg ttaacaaaac agttgttcct
aaagtgtctg gatatcaatt tagggtgttt aaggtg SEQ.ID.NO: 94
>HPV81
cgcacc aaccttttt attatgggg cagttcccgc cttcttactg
tagggcatcc atattgtaca ttaactattg taccccaagg aaagcgttcc
actattccca aggtgtctgg gtatcagtac cgggtgtttc gtgtg SEQ.ID.NO: 95
>HPV82
cgc accggcatat attattatgc aggcagttcc agacttatta ccttaggaca
tccatatttt tcaatacccca aaccaatac acgtgctgaa atacctaagg
tatctgcctt tcagtatagg gtgtttaggg ta SEQ.ID.NO: 96
>HPV83
cg caccaacctc ttttattacg gtggcagctc cagacttctt accgtaggac
atccatatta tcctgtacag gttaatggtc aaggaaaaaa agccactatc
cccaaggttt ctggctacca atatagggtg tttcgcatt SEQ.ID.NO: 97
>HPV84
cgcaccaac ttatttatt atggtggtag ttctcgcctg cttactgtgg
gacatccata ttattctgtt cctgtgtcta ccccctgggca aaacaacaaa
aaggccacta tccccaaggt ttctgggtat caatacaggg tgtttagggt c APPENDIX 1-continued SEQ.ID.NO: 98
>HPV85
cgta ccagtacatt ttatcatgct ggcagctcta ggcttctaac cgttggacat
ccatactata aagttacctc aaatggaggc cgcaagcaag acattcctaa
agtgtctgcc tatcagtatc gagtgtttcg ggtt SEQ.ID.NO: 99
>HPV86
cgtaccaac ctattttatt atggtggtag ttcccgcttg cttactgtgg
gccatccata ttatcctgtt actgtttcct ccagccctgg acaaaacaac
aaaaaggcca atattcccaa ggtttcgggg tatcaataca gggtttttag
ggtg SEQ.ID.NO: 100
>HPV87
cgcaccaac ttattttatt atggtggcag ttctcgcctg cttactgtgg
gtcacccta ctatccagtt actgttacca ccctggtca gaacaagaaa
tccaatattc caaggtgtc tggctatcag tacagggtgt ttcgggtg SEQ.ID.NO: 101
>HPV89
cgtaccaac ctgtactatt atggaggcag ctcccgcctt attacagttg
gccacccta ttatactgta caggtcaatg gtgctaacaa aaaggccaac
atacctaagg tatcagggta tcaatacagg gtatttaggg ta SEQ.ID.NO: 102
>HPV90
agaacaaacata tattattatg caggcagttc ccgactgtta actgttggcc
atccttattt tgctatcaaa aagcaatcag gaaaaaaccc tatagtggtt
cccaaggtgt ctggatatca atagggtg tttagggta SEQ.ID.NO: 103
>HPV91
cgcacc aacttatttt accatgctgg cagttcccgt ttactggctg
tgggccaccc ttttttttcct ataaaaaata attctggtaa agtaattgtt
cctaaagttt caggtcacca atatagggtg tttagagtt SEQ.ID.NO: 104
HPV-IC
CGGACGAATGTTTATTACCAGATAGATAGAGATAGATACCCATATACAGATAATGACATA
GATCCCCATAGACAGTTTATACAGATCAGTAGCAGTTTTTATATATGAGATGATGATAGC
AATACAGAGTATTTAGGGTA

| SEQ.ID.NO: 105 | HPV11B3/2: | AAAACAGTTGTACCAAAGGTGTCTG |
|---|---|---|
| SEQ.ID.NO: 106 | HPV42B1: | CAAAAAGGCCAAATAAGACA |
| SEQ.ID.NO: 107 | HPV43B6: | CCCCCTTAAAAATTCCTCT |
| SEQ.ID.NO: 108 | HPV44/55B1 | ATACGACCAGCAAACAAGAC |
| SEQ.ID.NO: 109 | HPV39B4: | TATGAATGGTGGTCGCAAG |
| SEQ.ID.NO: 110 | HPV52B7: | AAAACACCAGTAGTGCTAATG |
| SEQ.ID.NO: 111 | HPV56B3: | CCAAAACAAACATTCCCAA |
| SEQ.ID.NO: 112 | HPV59B3: | ATCCATATTTTAAAGTACCTAAAG |
| SEQ.ID.NO: 113 | HPV66B1: | CAAATCTGGTACCAAAACAAA |
| SEQ.ID.NO: 114 | HPV-ICB4: | CCCATAGACAGTTTATACAGATCA |
| SEQ.ID.NO: 115 | HPV6B6: | ATAAAACGGGCTAACAAAA |
| SEQ.ID.NO: 116 | HPV26B1: | TACCTAAAACTGGCCAAAAG |
| SEQ.ID.NO: 117 | HPV35B4: | ATTCTAATAAAATAGCAGTACCCAAG |

The invention claimed is:

1. A method of detecting the presence of at least one human papillomavirus (HPV) genotype comprising contacting a nucleic acid obtained from a sample with a set comprising at least four probes wherein each of said probes comprises a sequence complementary to a sequence from a HPV which is flanked on each end by a stem sequence, each stem sequence consisting of four or five pairs of complementary bases, wherein said bases form a stem structure in the absence of hybridization to a nucleic acid from the HPV, and wherein each of said probes is labeled with a first interacting label and a second interacting label such that hybridizing of a probe to a nucleic acid from the HPV causes a change in the signal detected, and
wherein said nucleic acid obtained from said sample is amplified utilising a primer mixture comprising SEQ ID NO:16.

2. The method as claimed in claim 1 wherein said nucleic acid obtained from said sample is amplified utilising a primer mixture further comprising SEQ ID NOS:1-15 and 17-32.

* * * * *